US00RE42930E

(19) United States
(12) Reissued Patent
Vite et al.

(10) Patent Number: US RE42,930 E
(45) Date of Reissued Patent: Nov. 15, 2011

(54) AZIRIDINYL-EPOTHILONE COMPOUNDS

(75) Inventors: Gregory D. Vite, Titusville, NJ (US); Soong-Hoon Kim, Titusville, NJ (US)

(73) Assignee: Bristol-Myers Squibb Company, Princeton, NJ (US)

(21) Appl. No.: 13/089,067

(22) Filed: Apr. 18, 2011

Related U.S. Patent Documents

Reissue of:

(64) Patent No.: 7,872,145
Issued: Jan. 18, 2011
Appl. No.: 11/753,785
Filed: May 25, 2007

U.S. Applications:

(60) Provisional application No. 60/808,366, filed on May 25, 2006.

(51) Int. Cl.
*C07D 277/22* (2006.01)
*C07D 203/26* (2006.01)

(52) U.S. Cl. ..... 548/202; 548/962

(58) Field of Classification Search ..... None
See application file for complete search history.

(56) References Cited

U.S. PATENT DOCUMENTS

| | | | | |
|---|---|---|---|---|
| 5,416,016 | A | 5/1995 | Low et al. | |
| 6,291,673 | B1 | 9/2001 | Fuchs et al. | |
| 6,291,684 | B1 | 9/2001 | Borzilleri et al. | |
| 6,399,638 | B1 * | 6/2002 | Vite et al. | 514/366 |
| 6,800,653 | B2 * | 10/2004 | Rugueiro-Ren et al. | 514/365 |
| 2005/0002942 | A1 | 1/2005 | Vlahov et al. | |

FOREIGN PATENT DOCUMENTS

| | | |
|---|---|---|
| WO | 00/66091 | 11/2000 |
| WO | 02/098868 | 12/2002 |
| WO | 2004/012735 | 2/2004 |
| WO | 2004/054622 | 7/2004 |
| WO | 2005/074901 | 8/2005 |
| WO | 2006/042146 | 4/2006 |

OTHER PUBLICATIONS

Regueiro-Ren et al. Organic Letters, 2001, vol. 3, No. 17, pp. 2693-2696.*
Melby, et al., "Entry of Protein Toxins in Polarized Epithelial Cells", Cancer Research., vol. 53 (1993) 1755-60.
Olsnes, et al., "Immunotoxins entry cells and mechanisms of action", Immunology Today, vol. 10, No. 9 (1989) 291-95.
Regueiro-Ren, et al., "Synthesis and Biological Activity of Novel Epothilone Aziridines", Organic Letters, vol. 3, No. 17 (2001) 2693-96.
Kamen, et al., "A review of folate receptor alpha cycling and 5-methyltetrahydrofolate accumulation with an emphasis on cell models in vitro", Advanced Drug Delivery Reviews, vol. 56 (2004) 1085-97.
Jackman, et al., "Antifolates targeted specifically to the folate receptor", Advanced Drug Delivery Reviews, vol. 56 (2004) 1111-25.
Elnakat, et al., "Distribution, functionality and gene regulation of folate receptor isoforms: implication in targeted therapy", Advanced Drug Delivery Reviews, vol. 56 (2004) 1067-84.
Sabharanjak, et al., "Folate receptor endocytosis and trafficking", Advanced Drug Delivery Reviews, vol. 56 (2004) 1099-1109.
Paulos, et al., "Folate receptor-mediated targeting of therapeutic and imaging agents to activated macrophages in rheumatoid arthritis", Advanced Drug Delivery Reviews, vol. 56 (2004) 1205-17.
Antony, "Folate receptors: reflections on a personal odyssey and a perspective on unfolding truth", Advanced Drug Delivery Reviews, vol. 56 (2004) 1059-66.
"Folate Receptor-Targeted Drugs for Cancer and Inflammatory Diseases", Advanced Drug Delivery Reviews, vol. 56 (2004) vol. 56, No. 8 (2004) 1055-58.
Lu, et al., "Folate receptor-targeted immunotherapy of cancer: mechanism and therapeutic potential", Advanced Drug Delivery Reviews, vol. 56 (2004) 1161-76.
Roy, et al., "Folate-mediated targeting of T cells to tumors", Advanced Drug Delivery Reviews, vol. 56 (2004) 1219-31.
Ke, et al., "Folate-receptor-targeted radionuclide imaging agents", Advanced Drug Delivery Reviews, vol. 56 (2004) 1143-60.
Leamon, et al., "Folate-targeted chemotherapy", Advanced Drug Delivery Reviews, vol. 56 (2004) 1127-41.
Gabizon, et al., "Tumor cell targeting of liposome-entrapped drugs with phospholipid-anchored folic acid-PEG conjugates", Advanced Drug Delivery Reviews, vol. 56 (2004) 1177-92.
Zhao, et al., "Tumor-selective targeted delivery of genes and antisense oligodeoxyribonucleotides via the folate receptor", Advanced Drug Delivery Reviews, vol. 56 (2004) 1193-1204.

* cited by examiner

*Primary Examiner* — Rebecca Anderson
*Assistant Examiner* — Alicia L Otton
(74) *Attorney, Agent, or Firm* — Yuan Chao; Anastasia Winslow; Laurelee Duncan

(57) ABSTRACT

The present invention is directed to aziridinyl epothilone compounds as further described herein, and/or pharmaceutically-acceptable salts and/or solvates thereof having the following Formula:

wherein K is —O—, —S—, or —$NR_7$—; A is —$(CR_8R_9)$—$(CH_2)_m$—Z—wherein Z is —$(CHR_{10})$—, —C(=O)—, —C(=O)—C(=O)—, —OC(=O)—, —$N(R_{11})$C(=O)—, —$O_2$—, or —$N(R_{11})SO_2$—; $B_1$ is hydroxyl or cyano and $R_1$ is hydrogen or $B_1$ and $R_1$ are taken together to form a double bond; $R_2$, $R_3$, and $R_5$ are, independently, hydrogen, alkyl, substituted alkyl, aryl or substituted aryl; or $R_2$ and $R_3$ may be taken together with the carbon to which they are attached to form an optionally substituted cycloalkyl; $R_4$ is hydrogen, alkyl, alkenyl, substituted alkyl, substituted alkenyl, aryl, or substituted aryl; $R_6$ is hydrogen, alkyl or substituted alkyl; $R_7$, $R_8$, $R_9$, $R_{10}$, $R_{11}$ and $R_{12}$ are independently hydrogen, alkyl, substituted alkyl, cycloalkyl, substituted cycloalkyl, aryl, substituted aryl, heterocycloalkyl, substituted heterocycloalkyl, heteroaryl, or substituted heteroaryl; and $R_{13}$ is aryl, substituted aryl, heteroaryl or substituted heteroaryl.

10 Claims, 6 Drawing Sheets

| Conjugate Number | Relative Affinity | EC50(nM) KB cells | Structure |
|---|---|---|---|
| AA.I | 0.27 | >100 | 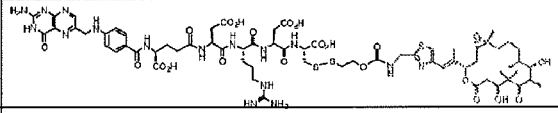 |
| AA.II | 0.29 | >100 | 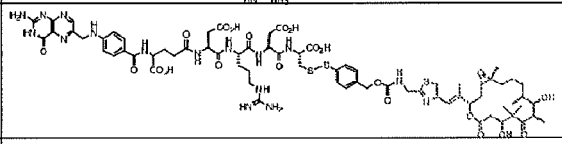 |
| AA.III | n.t. | >100 | 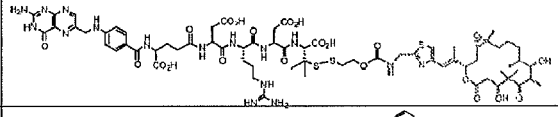 |
| AA.IV | n.t. | 50 | 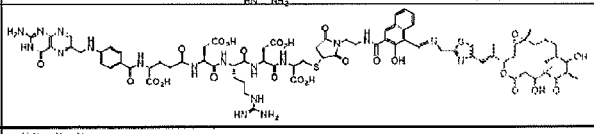 |
| AA.V | n.t. | >100 | 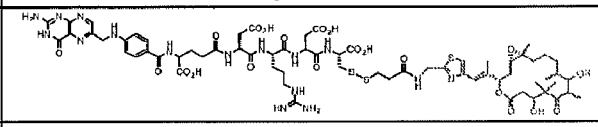 |
| AA.VI | n.t. | >100 | 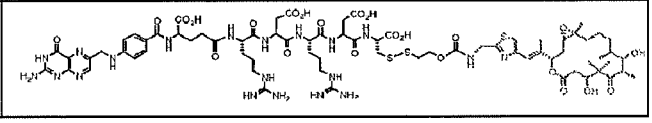 |
FIG. 1

| Conjugate Number | Relative Affinity | EC50(nM) KB cells | Structure |
|---|---|---|---|
| BB.I | n.t. | 68 | 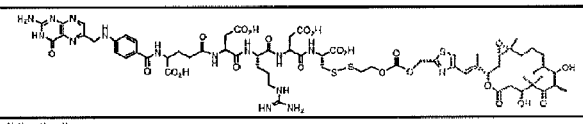 |
| BB.II | 0.13 | 10-100 (decomposition to free epothilone) | 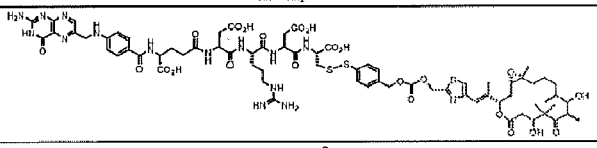 |
| BB.III | n.t. | ~75 | 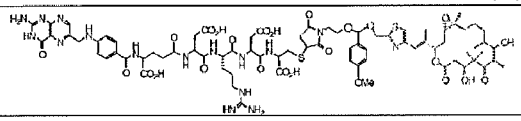 |
FIG. 2

FIG. 4A Efficacy*
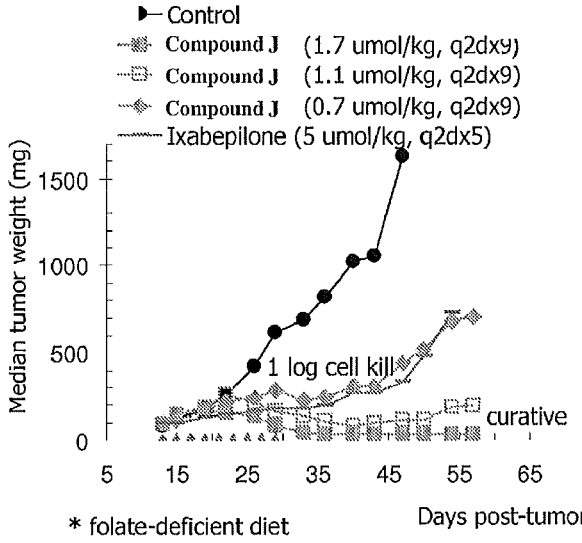
* folate-deficient diet
FIG. 4B Weight Loss*
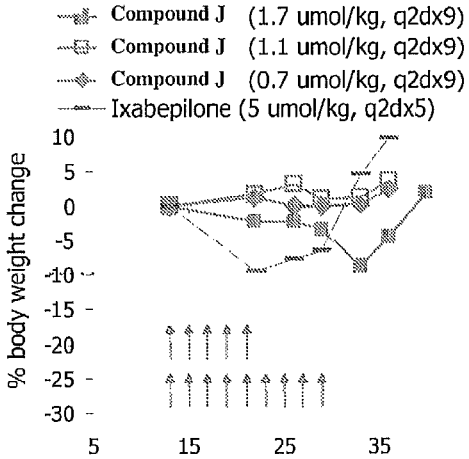

AZIRIDINYL-EPOTHILONE COMPOUNDS

Matter enclosed in heavy brackets [ ] appears in the original patent but forms no part of this reissue specification; matter printed in italics indicates the additions made by reissue.

This application claims priority to U.S. Provisional Patent Application No. 60/808,366, filed May 25, 2006, which is hereby incorporated by reference herein in its entirety.

BACKGROUND OF THE INVENTION

1. Field of the Invention

The present invention relates to aziridinyl-epothilone analogs pharmaceutical compositions comprising aziridinyl-epothilone analogs, and methods of using the same.

2. Related Background Art

Epothilones A and B are naturally-occurring compounds that were discovered by Höfle et al. as isolated from fermentation products of the microorganism, Sorangium cellulosum (see, e.g., WO 93/10121). Höfle et al. also discovered 37 natural epothilone variants and related compounds produced by Sorangium cellulosum, including epothilones C, D, E, F and other isomers and variants. See, e.g., U.S. Pat. No. 6,624,310. While in 1993 Höfle et al reported on cytotoxic effects of Epothilones A and B, in 1995 researchers with Merck reported that epothilone B exerts microtubule-stabilizing effects similar to paclitaxel (TAXOL®) (See D. M. Bollag, "Epothilones, a New Class of Microtubule-Stabilizing Agents with a Taxol-like Mechanism of Action," Cancer Research, Vol. 55 (June 1995), at pp. 2325-2333).

Various derivatives and analogs of the naturally-occurring epothilones have been discovered at Bristol-Myers Squibb Co. Examples of epothilone analogs include the aza-epothilone B analog known as ixabepilone, 21-substituted analogs of epothilone B including a 21-amino analog, 2,3-olefinic analogs, C-3 cyano analogs, cyclopropyl analogs, and heterocyclic analogs including aziridinyl-epothilone analogs. See, e.g. U.S. Pat. Nos. 6,605,599; 6,262,094; 6,399,638; 6,498,257; 6,380,395; and 6,800,653, each of which is incorporated herein by reference. Others have also reported on the discovery of other epothilone derivatives and analogs. See, e.g., PCT Pub. Nos. WO 99/65913, WO 98/25929; WO 00/99/07692; WO 99/67252; WO 00/00485; WO 00/37473; WO 01/83800; WO 99/67253, WO 99/07692, WO 00/00485, WO 00/49021, WO 00/66589, WO 03/045324, WO 04/014919, WO 04/056832, WO 03/022844; U.S. Pat. Nos. 6,441,186; 6,284,781; 6,660,758; 6,380,394; 6,242,469; 6,531,497; 6,441,186; 6,489,314; 6,589,968; 6,930,102; US Pat. Appl. Pub. Nos. US 2004/0072870 A1; US 2003/0023082 A1; US 2004/0053910 A1; US 2004/0152708 A1, all of which are incorporated by reference in their entirety.

The naturally-occurring epothilones and their analogs, like other microtubule-stabilizing agents, may be useful for treating proliferative diseases such as cancer, which typically work by killing (or arresting the growth of) tumor cells, other pathogenic cells, and foreign pathogens. Often, however, anticancer drugs attack not only tumor cells but also normal tissue, leading to undesired side effects. Additionally, anticancer drugs typically present solubility issues such that formulation and delivery of the agents can present challenges, leading to use of solubilizing agents such as CREMOPHOR®. The cytotoxicity of some anticancer drugs and/or formulation ingredients has been known to cause neuropathy or other side effects such as hypersensitivity reactions. These adverse side effects highlight the need for anticancer therapies that are selective for pathogenic cell populations and therefore result in reduced host toxicity.

However, as discussed in WO 2004/054622 A1 scientists have for many years attempted to use monoclonal antibodies (mAbs) in targeted drug therapies for delivery of chemotherapeutic agents to patients, but drawbacks have been encountered in terms of, inter alia, the cleavable moiety, the linkers, and the form of drug released in the cell. It has been reported that successful therapy of tumors with mAbs is limited by inadequate penetration of the antibody in the tumor and by the heterogeneous distribution of corresponding tumor-associated antigen in the tumor tissue. See, Klar et al., WO 05/074901 (assigned to Schering AG).

US Pat. App. Pub. No. 2005/0002942 discloses vitamin receptor binding drug delivery conjugates that are useful for targeted drug delivery. There is a need in the art for identifying anticancer agents that could be used to make conjugates such as those described in US 2005/0002942, in the interest of providing targeted drug delivery for cancer treatment.

SUMMARY OF THE INVENTION

The present invention is directed to compounds having the following Formula X:

X

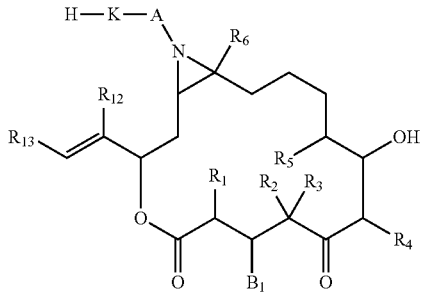

or pharmaceutically-acceptable salts and/or solvates thereof, wherein:

K is —O—, —S—, or —$NR_7$—;

A is —($CR_8R_9$)—$(CH_2)_m$-Z- wherein Z is —($CHR_{10}$)—, —C(═O)—, —C(═O)—C(═O)—, —OC(═O)—, —N($R_{11}$)C(═O)—, —$SO_2$—, or —N($R_{11}$)$SO_2$—;

$B_1$ is hydroxyl or cyano and $R_1$ is hydrogen or $B_1$ and $R_1$ are taken together to form a double bond;

$R_2$, $R_3$, and $R_5$ are, independently, hydrogen, alkyl, substituted alkyl, aryl or substituted aryl; or $R_2$ and $R_3$ may be taken together with the carbon to which they are attached to form an optionally substituted cycloalkyl;

$R_4$ is hydrogen, alkyl, alkenyl, substituted alkyl, substituted alkenyl, aryl, or substituted aryl;

$R_6$ is hydrogen, alkyl or substituted alkyl;

$R_7$, $R_8$, $R_9$, $R_{10}$, and $R_{11}$ are independently hydrogen, alkyl, substituted alkyl, cycloalkyl, substituted cycloalkyl, aryl, substituted aryl, heterocycloalkyl, substituted heterocycloalkyl, heteroaryl, or substituted heteroaryl;

$R_{12}$ is H, alkyl, substituted alkyl, or halogen;

$R_{13}$ is aryl, substituted aryl, heteroaryl or substituted heteroaryl; and m is 0 to 6.

The present invention is further directed to methods for treating cancer with use of compounds having the Formula X, as well as use of the compounds of Formula X in preparing pharmaceutical compositions with pharmaceutically acceptable carriers for treating cancer. Compounds of Formula X are especially useful in preparing compositions for targeted drug therapies.

BRIEF DESCRIPTION OF THE DRAWINGS

FIG. 1 is the chemical structures, relative affinities, and EC50 (nM) values against KB tumor cells of six folate conjugates of epothilone analog Compound AA (conjugate number AA.I to AA-VI).

FIG. 2 is the chemical structures, relative affinities, and EC50 (nM) values against KB tumor cells of three folate conjugates of epothilone analog Compound BB (conjugate number BB.I to BB.III).

FIG. 4 demonstrates the in vivo antitumor efficacy of treating KB nasopharyngeal epidermoid carcinoma xenografts in nude mice with Compound J (grey squares, white squares, grey diamonds) at various doses or ixabepilone (black bars), compared to no treatment (control; black circles), as a measure of (A) median tumor weight (mg; y-axis) several days post tumor implant (x-axis) or (B) weight loss (% body weight change; y-axis) several days post-tumor implant (x-axis).

DETAILED DESCRIPTION OF THE INVENTION

Definitions of Terms

Figure 3:
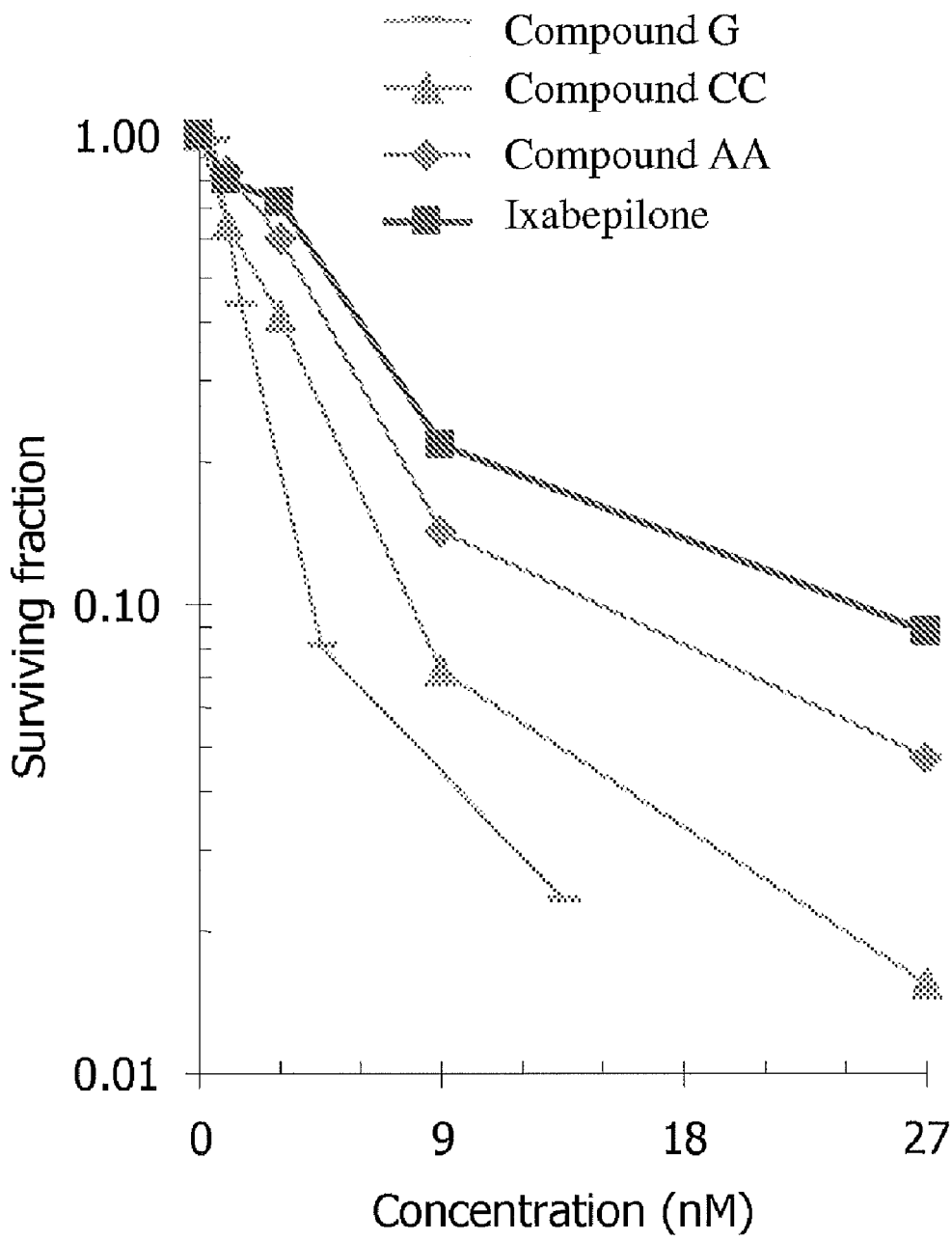
FIG. 3 demonstrates the fraction of surviving KB clones (Surviving fraction; y-axis) after treatment with increasing concentrations (Concentration (nM); x-axis) of Compound G (bars), Compound CC (triangles), Compound AA (diamonds), or ixabepilone (squares).

The following are definitions of terms used in the present specification. The initial definition provided for a group or term herein applies to that group or term throughout the present specification individually or as part of another group, unless otherwise indicated.

The term "folate-binding moiety or analog or derivative thereof" as used herein means a moiety that will bind to a folate-receptor protein (not a monoclonal antibody) that is overexpressed or preferentially expressed on cancer cells. For example, it is known that the folate receptor (FR) is overexpressed in ovarian cancer cells and other cancer cells. Illustrative analogs and derivatives of folate are disclosed in US Pat. App. Pub. No. 2005/0002942 to Vlahov et al., (hereinafter "Vlahov"), incorporated herein by reference.

The term "releasable linker" as used herein means a bivalent linker that includes at least one cleavable bond that can be broken under physiological conditions (e.g. a pH-labile, reductively-labile, acid-labile, oxidatively-labile, or enzyme-labile bond.) It should be appreciated that such physiological conditions resulting in bond breaking include standard chemical hydrolysis reactions that occur, for example, at physiological pH, or as a result of compartmentalization into a cellular organelle, such as an endosome having a lower pH than cytosolic pH, or as a result of reaction with a cellular reducing agent such as glutathione.

It is understood that a cleavable bond can connect two adjacent atoms within the releasable linker and/or connect other groups to the releasable linker such as Q and K, as described herein, at either or both ends of the linker.

The terms "alkyl" and "alk" whether alone or in combination with some other group, refer to a straight or branched chain alkane (hydrocarbon) radical attached at any available carbon atom, containing from 1 to 10 carbon atoms, preferably 1 to 6 carbon atoms, more preferably from 1 to 4 carbon atoms. Exemplary such groups include, but are not limited to methyl, ethyl, propyl, isopropyl, n-butyl, t-butyl, isobutyl, pentyl, hexyl, heptyl, 4,4-dimethylpentyl, octyl, 2,2,4-trimethylpentyl, and the like. "Lower alkyl" or "lower alkylene" means a straight or branched chain alkyl having one to four carbon atoms. When a subscript is used with reference to an alkyl or other group, the subscript refers to the number of carbon atoms that the group may contain. For example, the term "$C_{0-4}$alkyl" includes a bond and alkyl groups of 1 to 4 carbon atoms, and the term "$C_{1-4}$alkyl" means alkyl groups of 1 to 4 carbon atoms.

The term "alkylene" refers to a bivalent hydrocarbon radical, as described above for "alkyl" but with two points of attachment. For example, a methylene group is a —$CH_2$— group and an ethylene group is a —$CH_2$—$CH_2$— group.

When the term alkyl is used in connection with another group, as in heterocycloalkyl or cycloalkylalkyl, this means the other identified (first named) group is bonded directly through an alkyl group as defined above (e.g., which may be branched or straight chain). Thus, the term "alkyl" is used in this instance to refer to an alkylene, e.g., a divalent alkyl group, having two available points of attachment. For example, cyclopropyl $C_{1-4}$alkyl means a cyclopropyl group bonded through a straight or branched chain alkylene having one to four carbon atoms, and hydroxyalkyl means the group OH bonded through a straight or branched chain alkylene having one to ten carbon atoms, preferably 1 to 6 carbon atoms, more preferably 1 to 4 carbon atoms. In the case of substituents, as in "substituted cycloalkylalkyl," the alkylene portion of the group, besides being branched or straight chain, may be substituted as recited below for substituted alkyl groups and/or the first named group (e.g., cycloalkyl) may be substituted as recited herein for that named group (e.g., cycloalkyl).

"Substituted alkyl" refers to an alkyl group substituted with one or more substituents, preferably 1 to 4 substituents, at any available point of attachment. However, when an alkyl group is substituted with multiple halo substituents, the alkyl may contain as valence allows up to 10 substituents, more preferably up to seven substituents. Alkyl substituents may include one or more of the following groups: halo (e.g., a single halo substituent or multiple halo substituents forming, in the latter case, groups such as a perfluoroalkyl group or an alkyl group bearing $Cl_3$ or $CF_3$), cyano, —$R_a$, —$SR_a$, —C(═O)$R_a$, —C(═O)O$R_a$, —OC(═O)$R_a$, —OC(═O)O$R_a$, —N$R_a$$R_b$, —C(═O)N$R_a$$R_b$, —OC(═O)N$R_a$$R_b$, —S(═O)$R_a$, —S(O)$_2$$R_a$, —NHS(O)$_2$$R_a$, —NHS(O)$_2$NH$R_a$, —NHC(═O)NH$R_a$, —NHC(═O)$R_a$, —NHC(O)$_2$$R_a$, —NHC(═N—CN)$R_a$, aryl, heterocycle, cycloalkyl, and/or heteroaryl, wherein the groups $R_a$ and $R_b$ are independently selected from hydrogen, alkyl, alkenyl, cycloalkyl, heterocyclo, aryl, and heteroaryl, and wherein each $R_a$ and/or $R_b$ in turn is optionally substituted with one to four groups selected from alkyl, alkenyl, halogen, haloalkyl, haloalkoxy, cyano, nitro, amino, alkylamino, aminoalkyl, hydroxy, hydroxyalkyl, alkoxy, thiol, alkylthio, phenyl, benzyl, phenyloxy, benzyloxy, $C_{3-7}$cycloalkyl, five or six membered heterocyclo or heteroaryl, and/or a lower alkyl or lower alkenyl substituted with one to four groups selected from hydroxy, cyano, halogen, halo$C_{1-4}$alkyl, halo$C_{1-4}$alkoxy, cyano, nitro, amino, $C_{1-4}$alkylamino, amino$C_{1-4}$alkyl, hydroxy$C_{1-4}$alkyl, $C_{1-4}$alkoxy, thiol, and/or $C_{1-4}$ alkylthio. For the avoidance of doubt, a "substituted lower alkyl" means an alkyl group having one to four carbon atoms and one to four substituents selected from those recited immediately above for substituted alkyl groups. In the case of a substituted lower alkyl, preferably the groups $R_a$ and $R_b$ are selected from hydrogen, lower alkyl, lower alkenyl, $C_{3-7}$cycloalkyl, phenyl, and five to six membered monocyclic heterocyclo and/or heteroaryl, in turn optionally substituted as above.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include alkyl, substituted alkyl, and those groups recited above as alkyl substituents.

The terms "alkoxy" and "alkylthio" refer to an alkyl group as described above bonded through an oxygen linkage (—O—) or a sulfur linkage (—S—), respectively. The terms "substituted alkoxy" and "substituted alkylthio" refer to a substituted alkyl group as described above bonded through an oxygen or sulfur linkage, respectively. A "lower alkoxy" or a $C_{1-4}$alkoxy is a group OR, wherein R is lower alkyl (alkyl of 1 to 4 carbon atoms).

"Amino" is $NH_2$. An alkylamino is —$NR_cR_d$ wherein at least one of $R_c$ and $R_d$ is an alkyl or substituted alkyl, and the other of $R_c$ and $R_d$ is selected from hydrogen, alkyl, and substituted alkyl. An "aminoalkyl" means an amino group bonded through an alkylene group (-alkylene-$NH_2$), and an alkylaminoalkyl means an alkylamino as defined above bonded through an alkylene group (-alkylene-$NR_cR_d$).

The term "aryl" refers to cyclic, aromatic hydrocarbon groups which have 1 to 3 aromatic rings, especially monocyclic or bicyclic groups such as phenyl or naphthyl. Aryl groups which are bicyclic or tricyclic must include at least one fully aromatic carbocyclic ring but the other fused ring or rings may be aromatic or non-aromatic and may optionally contain heteroatoms, provided that in such cases the point of attachment will be to the aromatic carbocyclic ring. Additionally, when an aryl group has fused thereto a heterocyclic or cycloalkyl ring, the heterocyclic and/or cycloalkyl ring may have one or more carbonyl carbon atoms, i.e., attached via a double bond to an oxygen atom to define a carbonyl group. Thus, examples of "aryl" may include without limitation:

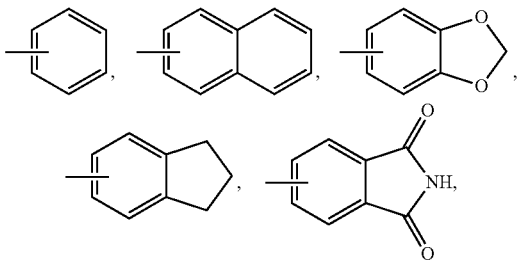

-continued

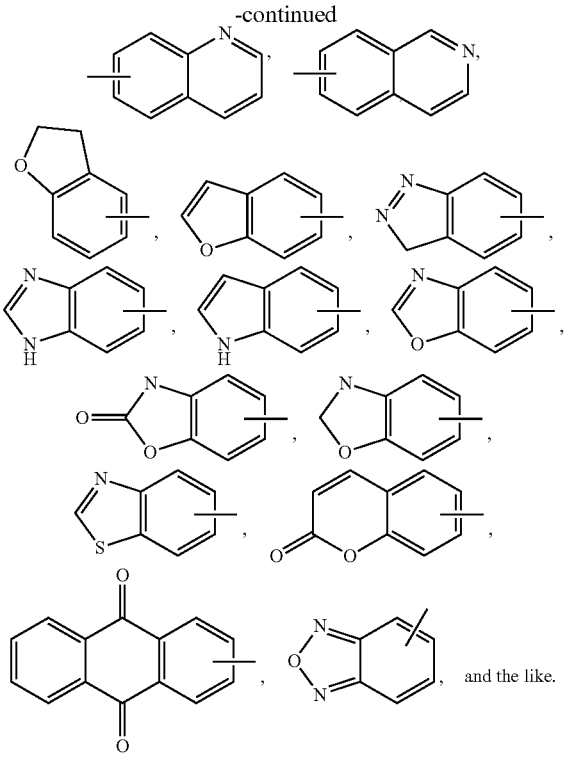

and the like.

The term "arylene" refers to a bivalent aryl radical, i.e., an aryl group as defined above having two points of attachment to two other groups, at any available points of attachment of the aryl ring. Arylene rings may also be substituted with any of the groups suitable for substitution on the aryl groups defined herein.

"Substituted aryl" refers to an aryl or arylene group as defined above substituted by one or more substituents, preferably 1 to 4 substituents, at any point of attachment. Substituents include alkyl, substituted alkyl, alkenyl, substituted alkenyl, as well as those groups recited above as alkyl substituents.

The term "carbocyclic" means a saturated or unsaturated monocyclic, bicyclic, or tricyclic ring (preferably mono- or bicyclic) in which all atoms of all rings are carbon. Thus, the term includes cycloalkyl and aryl rings. The carbocyclic ring may be substituted in which case the substituents are selected from those recited above for cycloalkyl and aryl groups.

The term "cycloalkyl" refers to a fully saturated or partially saturated cyclic hydrocarbon group containing from 1 to 3 rings and 3 to 7 carbon atoms per ring. Exemplary fully saturated cycloalkyl groups include cyclopropyl, cyclobutyl, cyclopentyl, and cyclohexyl. Exemplary partially saturated cycloalkyl groups include cyclobutenyl, cyclopentenyl, and cyclohexenyl. The term "cycloalkyl" includes such groups having a bridge of three to four carbon atoms. Additionally, cycloalkyl groups which are bicyclic or tricyclic must include at least one fully saturated or partially saturated hydrocarbon ring but the other fused ring or rings may be aromatic or non-aromatic and may contain heteroatoms, provided that in such cases the point of attachment will be to the cyclic, non-aromatic hydrocarbon group. Additionally, one or more carbon atoms of the cycloalkyl group may form a carbon-to-oxygen double bond to define a carbonyl group. Thus, examples of "cycloalkyl" groups may include, without limitation:

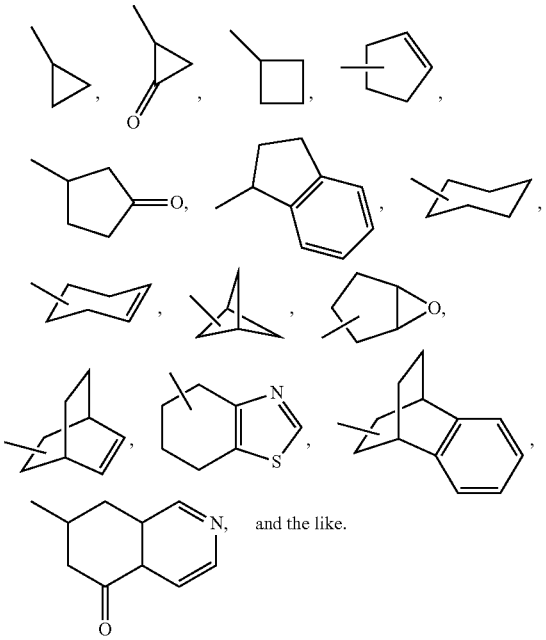

and the like.

The term "cycloalkylene" refers to a bivalent cycloalkyl radical, i.e., a cycloalkyl group as defined above having two points of attachment to two other groups, at any available two points of attachment of the cycloalkyl ring.

"Substituted cycloalkyl" refers to a cycloalkyl group as defined above substituted at any available point of attachment with one or more substituents, preferably 1 to 4 substituents. Cycloalkyl substituents include alkyl, substituted alkyl, alkenyl, substituted alkenyl, and those groups recited above as alkyl substituents.

The term "guanidinyl" means the group

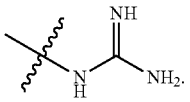

Thus, a guanidinylalkyl means an alkyl group bonded to the guanidinyl such as a group having the formula,

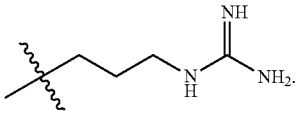

The term "halogen" or "halo" refers to fluorine, chlorine, bromine and iodine.

The term "heteroatoms" includes oxygen, sulfur and nitrogen.

The term "haloalkyl" means an alkyl having one or more halo substituents, including without limitation groups such as —$CH_2F$, —$CHF_2$ and —$CF_3$.

The term "haloalkoxy" means an alkoxy group having one or more halo substituents. For example, "haloalkoxy" includes —$OCF_3$.

When the term "unsaturated" is used herein to refer to a ring or group, the ring or group may be fully unsaturated or partially unsaturated.

The term "heteroaryl" refers to an aromatic group which is a 4 to 7 membered monocyclic, 7 to 11 membered bicyclic, or 10 to 15 membered tricyclic ring system, which has at least one ring containing at least one heteroatom. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic and may be carbocyclic, provided that in such cases the point of attachment will be at any available nitrogen or carbon atom of an aromatic heteroatom-containing ring. Additionally, the definition of heteroaryl groups itself includes rings wherein one or more of the carbon atoms is attached via a double bond to an oxygen atom to define a carbonyl group (provided the heteroaryl group is aromatic) and also when a heteroaryl group has fused thereto a heterocyclic or cycloalkyl ring, the heterocyclic and/or cycloalkyl ring may have one or more carbonyl groups.

Exemplary monocyclic heteroaryl groups include pyrrolyl, pyrazolyl, pyrazolinyl, imidazolyl, oxazolyl, isoxazolyl, thiazolyl (i.e.,

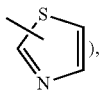

thiadiazolyl, isothiazolyl, furanyl, thienyl, oxadiazolyl, pyridyl, pyrazinyl, pyrimidinyl, pyridazinyl, triazinyl and the like. Additionally, since the definition of heteroaryl groups itself includes rings wherein one or more of the carbon atoms defines a carbonyl group, rings such as 2,4-dihydro-[1,2,4] triazol-3-one (i.e.,

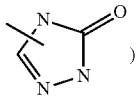

and the like are included.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzopyranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heteroalkylene" refers to a bivalent heteroaryl radical, i.e., a heteroaryl group as defined above having two points of attachment to two other groups, at any available two points of attachment of the heteroaryl ring.

"Substituted heteroaryl" groups are heteroaryl groups as defined above substituted with one or more substituents, preferably 1 to 4 substituents, at any available point of attachment. Exemplary substituents include, but are not limited to alkyl, substituted alkyl, alkenyl, substituted alkenyl, as well as those groups recited above as alkyl substituents.

The terms "heterocycle", "heterocyclic" and "heterocyclo" are used interchangeably and each refer to a fully saturated or partially unsaturated nonaromatic cyclic group, which may be substituted or unsubstituted, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen, oxygen, and sulfur atoms, where the nitrogen and sulfur heteroatoms also optionally may be oxidized and the nitrogen heteroatoms also optionally may be quatemized. Preferably two adjacent heteroatoms are not simultaneously selected from oxygen and nitrogen. Heterocyclic groups which are bicyclic or tricyclic must include at least one non-aromatic non-carbocyclic ring, but the other fused ring or rings may be aromatic or non-aromatic and may be carbocyclic, provided that in such cases the point of attachment will be at any available nitrogen or carbon atom of a non-aromatic heteroatom-containing ring. Additionally, the definition of heterocyclic groups itself includes rings wherein one or more of the carbon atoms is attached via a double bond to an oxygen atom to define a carbonyl group (provided the heterocyclic group is non-aromatic) and also when a heterocyclic group has fused thereto a further ring, such further ring may have one or more carbonyl groups.

Exemplary monocyclic heterocyclic groups include pyrrolidinyl, imidazolidinyl, tetrahydrofuryl, piperidinyl, piperazinyl, pyrazolidinyl, imidazolinyl, pyrrolinyl, tetrahydropyranyl, morpholinyl, thiamorpholinyl, and the like.

"Substituted heterocycle," "substituted heterocyclic," and "substituted heterocyclo" refer to heterocycle, heterocyclic, or heterocyclo groups as defined above substituted with one or more substituents, preferably 1 to 4 substituents, at any available point of attachment. Exemplary substituents include alkyl, substituted alkyl, alkenyl, substituted alkenyl, as well as those groups recited above as exemplary alkyl substituents.

"Hydroxy" refers to —OH.

"Thiol" means the group —SH.

The term "quaternary nitrogen" refers to a tetravalent positively charged nitrogen atom including, for example, the positively charged nitrogen in a tetraalkylammonium group (e.g., tetramethylammonium or N-methylpyridinium), the positively charged nitrogen in protonated ammonium species (e.g., trimethylhydroammonium or N-hydropyridinium), the positively charged nitrogen in amine N-oxides (e.g., N-methyl-morpholine-N-oxide or pyridine-N-oxide), and the positively charged nitrogen in an N-amino-ammonium group (e.g., N-aminopyridinium).

When a functional group is termed "protected", this means that the group is in modified form to mitigate, especially preclude, undesired side reactions at the protected site. Suitable protecting groups for the methods and compounds described herein include, without limitation, those described in standard textbooks, including Greene, T. W. et al., Protective Groups in Organic Synthesis, Wiley, N.Y. (1991), incorporated herein by reference.

Alternate Embodiments of the Invention

The present invention comprises compounds having the following Formula X, as set forth in the Summary of Invention.

The present invention comprises compounds having the stereospecific form according to Formula X'

X'

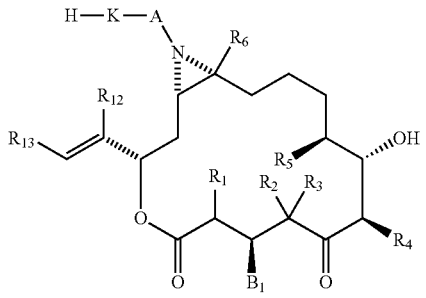

including pharmaceutically-acceptable salts and/or solvates thereof, wherein,

K is —O—, —S—, or —$NR_7$—;

A is —($CR_8R_9$)—($CH_2$)$_m$-Z- wherein Z is —($CHR_{10}$)—, —C(=O)—, —C(=O)—C(=O—)—, —OC(=O)—, —N($R_{11}$)C(=O)—, —$SO_2$—, or —N($R_{11}$)$SO_2$—;

$B_1$ is hydroxyl or cyano and $R_1$ is hydrogen or $B_1$ and $R_1$ are taken together to form a double bond;

$R_2$, $R_3$, and $R_5$ are, independently, hydrogen, alkyl, substituted alkyl, aryl or substituted aryl; or $R_2$ and $R_3$ may be taken together with the carbon to which they are attached to form an optionally substituted cycloalkyl;

$R_4$ is hydrogen, alkyl, alkenyl, substituted alkyl, substituted alkenyl, aryl, or substituted aryl;

$R_6$ is hydrogen, alkyl or substituted alkyl;

$R_7$, $R_8$, $R_9$, $R_{10}$, and $R_{11}$ are independently hydrogen, alkyl, substituted alkyl, cycloalkyl, substituted cycloalkyl, aryl, substituted aryl, heterocycloalkyl, substituted heterocycloalkyl, heteroaryl, or substituted heteroaryl;

$R_{12}$ is H, alkyl, substituted alkyl, or halogen;

$R_{13}$ is aryl, substituted aryl, heteroaryl or substituted heteroaryl; and m is 0 to 6.

In another embodiment, compounds of the invention have the Formula X

X

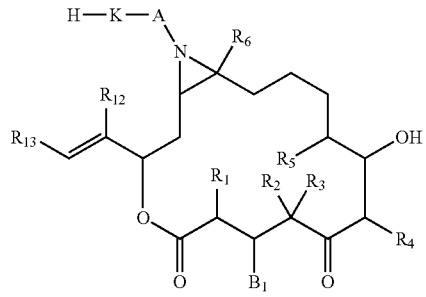

or the stereospecific Formula X', above, including pharmaceutically acceptable salts and/or solvates thereof, wherein K is —O—;

A is $C_{2-4}$ alkylene;

$B_1$ is —OH;

$R_2$, $R_3$, $R_4$ and $R_5$ are, independently, hydrogen or lower alkyl;

$R_6$ is hydrogen or methyl;

$R_{12}$ is H, alkyl, substituted alkyl, or halogen; and $R_{13}$ is an optionally substituted 5 or 6 membered heteroaryl.

In another embodiment, compounds of the invention have the Formula X or X', as defined above, including pharmaceutically acceptable salts and/or solvates thereof, wherein K is —O—;

A is $C_{2-4}$ alkylene;

$B_1$ is —OH;

$R_2$, $R_3$, $R_4$ and $R_5$ are, independently, hydrogen or lower alkyl;

$R_6$ is hydrogen;

$R_{12}$ is H, alkyl, substituted alkyl, or halogen; and $R_{13}$ is an optionally substituted 5 or 6 membered heteroaryl.

In another embodiment, compounds of the invention have the Formula X or X', as defined above, including pharmaceutically acceptable salts and/or solvates thereof, wherein K is —O—;

A is $C_{2-4}$ alkylene;

$B_1$ is —OH;

$R_2$, $R_3$, $R_4$ and $R_5$ are, independently, hydrogen or lower alkyl;

$R_6$ is hydrogen or methyl;

$R_{12}$ is H, alkyl, substituted alkyl, or halogen; and $R_{13}$ is an optionally substituted thiazolyl, pyridyl, or oxazolyl.

In another embodiment, compounds are provided having the formula Xa,

Xa

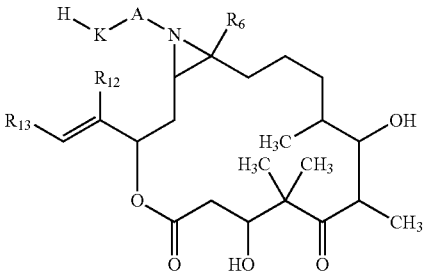

including pharmaceutically-acceptable salts and/or solvates thereof, wherein,

K is —O—, —S—, or —$NR_7$—;

A is —$(CR_8R_9)$—$(CH_2)_m$-Z- wherein Z is —$(CHR_{10})$—, —C(=O)—, —C(=O)—C(=O)—, —OC(=O)—, —$N(R_{11})$C(=O)—, —$SO_2$—, or —$N(R_{11})SO_2$—;

$R_6$ is hydrogen or methyl;

$R_8$, $R_9$, $R_{10}$, and $R_{11}$ are independently hydrogen, alkyl, or substituted alkyl, $R_{12}$ is H, alkyl, substituted alkyl, or halogen; and $R_{13}$ is aryl, substituted aryl, heteroaryl or substituted heteroaryl; and m is 0 to 6.

In another embodiment of the invention, compounds of formula Xa, including compounds of formula Xa' having the stereospecific form Xa', corresponding to the stereochemistry shown for X', are provided.

In another embodiment, compounds are provided having the formula Xa, or Xa', immediately above, wherein K is —O— and $R_{13}$ is optionally substituted thiazolyl, pyridyl, or oxazolyl, and the remaining groups are as defined above.

In another embodiment, compounds are provided having the formula Xa, or Xa', above, wherein K is —O—; A is $C_{2-4}$alkylene; $R_6$ is hydrogen or methyl; $R_{12}$ is H, lower alkyl, or halogen; and $R_{13}$ is optionally-substituted thiazolyl, pyridyl, or oxazolyl.

A compound of the invention may also have the formula Xb

Xb

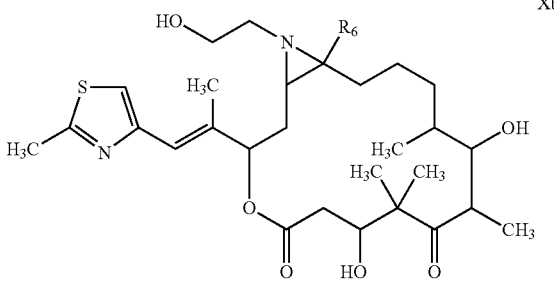

including pharmaceutically-acceptable salts and/or solvates thereof, wherein $R_6$ is hydrogen or methyl.

In another embodiment, a compound of the invention has the formula Xb, wherein $R_6$ is hydrogen.

In another embodiment, a compound of the invention may have the stereospecific formula Xb'

Xb'

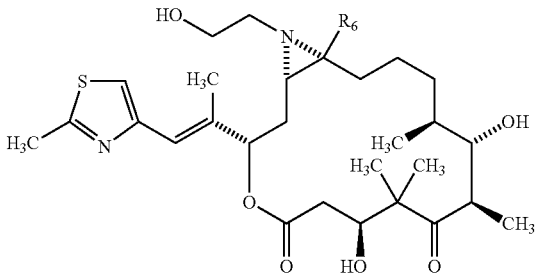

including pharmaceutically-acceptable salts and/or solvates thereof, wherein $R_6$ is hydrogen or methyl.

In another embodiment, a compound of the invention has the formula Xb', wherein $R_6$ is hydrogen.

According to one embodiment of the present invention, methods are provided for treating cancer, e.g., a folate-receptor associated condition, comprising treating a patient with a therapeutically effective amount of a compound having the following Formula X:

X

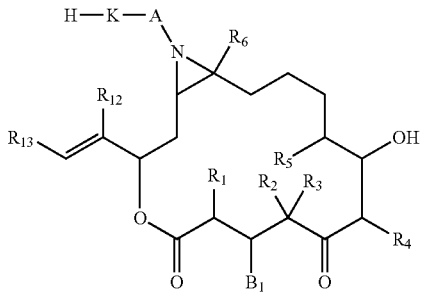

or a pharmaceutically-acceptable salt and/or solvate thereof, wherein:

K is —O—, —S—, or $NR_7$—;

A is —$(CR_8R_9)$—$(CH_2)_m$-Z- wherein Z is —$(CHR_{10})$—, —C(=O)—, —C(=O)—C(=O)—, —OC(=O)—, —$N(R_{11})$C(=O)—, —$SO_2$—, or —$N(R_{11})SO_2$—;

$B_1$ is hydroxyl or cyano and $R_1$ is hydrogen or $B_1$ and $R_1$ are taken together to form a double bond;

$R_2$, $R_3$, and $R_5$ are, independently, hydrogen, alkyl, substituted alkyl, aryl or substituted aryl; or $R_2$ and $R_3$ may be taken together with the carbon to which they are attached to form an optionally substituted cycloalkyl;

$R_4$ is hydrogen, alkyl, alkenyl, substituted alkyl, substituted alkenyl, aryl, or substituted aryl;

$R_6$ is hydrogen, alkyl or substituted alkyl;

$R_7$, $R_8$, $R_9$, $R_{10}$, and $R_{11}$ are independently hydrogen, alkyl, substituted alkyl, cycloalkyl, substituted cycloalkyl, aryl, substituted aryl, heterocycloalkyl, substituted heterocycloalkyl, heteroaryl, or substituted heteroaryl;

$R_{12}$ is H, alkyl, substituted alkyl, or halogen;

$R_{13}$ is aryl, substituted aryl, heteroaryl or substituted heteroaryl; and m is 0 to 6.

In one embodiment, the method comprises treating a patient with a therapeutically effective amount of a compound having the stereospecific Formula X',

X'

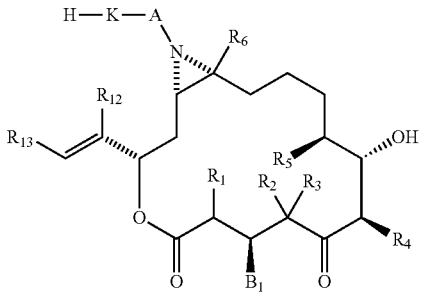

including pharmaceutically-acceptable salts and/or solvates thereof, wherein, wherein K, A, $B_1$ $R_1$, $R_2$, $R_3$, $R_4$, $R_5$, $R_6$, $R_7$, $R_8$, $R_9$, $R_{10}$, $R_{11}$ $R_{12}$, $R_{13}$, and m are as defined above for compounds of Formula X.

In another embodiment, the method comprises treating a patient with a therapeutically effective amount of a compound having the formula X, including formula X', as described above, including pharmaceutically acceptable salts and/or solvates thereof, wherein K is —O—;

A is $C_{2-4}$ alkylene;

$B_1$ is —OH;

$R_2$, $R_3$, $R_4$ and $R_5$ are, independently, hydrogen or lower alkyl;

$R_6$ is hydrogen or methyl;

$R_7$, $R_8$, $R_9$, $R_{10}$, and $R_{11}$ are independently hydrogen, alkyl, substituted alkyl, cycloalkyl, substituted cycloalkyl, aryl, substituted aryl, heterocycloalkyl, substituted heterocycloalkyl, heteroaryl, or substituted heteroaryl;

$R_{12}$ is H, alkyl, substituted alkyl, or halogen; and $R_{13}$ is an optionally substituted 5 or 6 membered heteroaryl.

In another embodiment, the method comprises treating a patient with a therapeutically effective amount of a compound having the formula X, or X', as described above, including pharmaceutically acceptable salts and/or solvates thereof, wherein K is —O—;

A is $C_{2-4}$ alkylene;

$B_1$ is —OH;

$R_2$, $R_3$, $R_4$ and $R_5$ are, independently, hydrogen or lower alkyl;

$R_6$ is hydrogen;

$R_7$, $R_8$, $R_9$, $R_{10}$, and $R_{11}$ are independently hydrogen, alkyl, substituted alkyl, cycloalkyl, substituted cycloalkyl, aryl, substituted aryl, heterocycloalkyl, substituted heterocycloalkyl, heteroaryl, or substituted heteroaryl;

$R_{12}$ is H, alkyl, substituted alkyl, or halogen; and $R_{13}$ is an optionally substituted 5 or 6 membered heteroaryl.

In another embodiment, the method comprises treating a patient with a therapeutically effective amount of a compound having the formula X, or X', as described above, including pharmaceutically acceptable salts and/or solvates thereof, wherein K is —O—;

A is $C_{2-4}$ alkylene;

$B_1$ is —OH;

$R_2$, $R_3$, $R_4$ and $R_5$ are, independently, hydrogen or lower alkyl;

$R_6$ is hydrogen or methyl;

$R_7$, $R_8$, $R_9$, $R_{10}$, and $R_{11}$ are independently hydrogen, alkyl, substituted alkyl, cycloalkyl, substituted cycloalkyl, aryl, substituted aryl, heterocycloalkyl, substituted heterocycloalkyl, heteroaryl, or substituted heteroaryl;

$R_{12}$ is H, alkyl, substituted alkyl, or halogen; and $R_{13}$ is an optionally substituted thiazolyl, pyridyl, or oxazolyl.

A method of the invention may also comprise treating a patient in need of such treatment with a therapeutically effective amount of a compound having the formula Xa, above, or the stereo specific form Xa', including pharmaceutically-acceptable salts and/or solvates thereof, wherein, K is —O—, —S—, or —$NR_7$—; A is —$(CR_8R_9)$—$(CH_2)_m$-Z- wherein Z is —$(CHR_{10})$—, —C(=O)—, —C(=O)—C(=O)—, —OC(=O)—, —$N(R_{11})$C(=O)—, —$SO_2$—, or —$N(R_{11})SO_2$—; $R_6$ is hydrogen or methyl; $R_8$ and $R_9$ are independently hydrogen, alkyl, or substituted alkyl, $R_{12}$ is H, alkyl, substituted alkyl, or halogen; $R_{13}$ is aryl, substituted aryl, heteroaryl or substituted heteroaryl; and m is 0 to 6.

A method of the invention may also comprise treating a patient in need of such treatment a therapeutically effective amount of a compound having the formula Xb or Xb', above, wherein $R_6$ is hydrogen or methyl. In yet another embodiment, the method comprises treating the patient with a compound of formula Xb or Xb', wherein $R_6$ is hydrogen.

Another embodiment of the invention comprises use of any of the compounds described above (including compounds of formula X, Xa, Xa', Xb, and/or Xb', wherein the groups K, A, $B_1$ $R_1$, $R_2$, $R_3$, $R_4$, $R_5$, $R_6$, $R_7$, $R_8$, $R_9$, $R_{10}$, $R_{11}$ $R_{12}$, and $R_{13}$ may be selected as recited above), in making pharmaceutical compositions for treating cancer in patients, particularly, for use in making pharmaceutical compositions containing conjugated compounds for targeted drug delivery to tumors that over-express or preferentially express the folate receptor.

Another embodiment of the invention comprises treating a patient in need of such treatment with a therapeutically effective amount of a compound having the formulas X, Xa, Xa', Xb, and/or Xb' (wherein the groups K, A, $B_1$ $R_1$, $R_2$, $R_3$, $R_4$, $R_5$, $R_6$, $R_7$, $R_8$, $R_9$, $R_{10}$, $R_{11}$ $R_{12}$, and $R_{13}$ may be selected as recited above), wherein the treatment occurs at the tumor site, having been released at the tumor site. In this embodiment, a conjugated compound is delivered to the tumor site, and then the compound of formulae X, Xa, Xa', Xb, or Xb', as defined above, is released at the tumor site and treats the patient at the tumor site. It is therefore understood herein, whenever the term "treatment" is used with reference to treating a patient, that this encompasses treatment at the tumor site, however delivered, e.g., via a conjugated compound.

The use of an agent to upregulate the level of folate receptor (FR) may be effective to increase the FR expression in certain cancer cells or tumor types to enhance the advantages obtained upon administering the compounds of the invention to patients, and/or to enhance the various diseases or tumor types that may be treated with the folate receptor binding compounds according to the invention. The expression of folate receptor in certain cancers may be upregulated by the administration of a folate receptor inducer, which selectively increases the level of folate receptor in the cancer cells, thus enhancing the effectiveness a folate receptor targeted therapy. For example, estrogen receptor positive (ER+) breast cancers express low levels of folate receptors. Treatment with a folate receptor inducer, such tamoxifen, an estrogen antagonist, is known to upregulate the expression of folate receptors in ER+ breast cancers, increasing the ER+ breast cancer cells susceptibility to treatment with a folate receptor targeted therapy.

One aspect of the invention provides a method of treating cancer or a proliferative disease in a patient, comprising optionally administering to a patient an effective amount of at least one folate receptor inducer, and treating the patient with an effective amount of at least one compound according to formula X. The folate receptor inducer may be administered before, during, or after the patient is treated with the compound according to formula X. In one embodiment, the folate receptor inducer is administered prior to treatment with the compound of formula X. An effective amount of the folate receptor inducer refers to an amount that upregulates the folate receptor in the desired cells such that the treatment with the compound is therapeutically effective.

Examples of folate receptor inducers for the upregulation of folate receptor α (FRα) include: estrogen receptor antagonists such as tamoxifen; progesterone receptor agonists such as progestin; androgen receptor agonists such as testosterone and dihydroxytestosterone, and glucocorticoid receptor agonists such as dexamethasone.

Examples of folate receptor inducers for the upregulation of folate receptor β (FRβ) include: retinoic acid receptor agonists such as all-trans retinoic acid (ATRA), tetramethyl napthalenyl propenyl benzoic acid (TTNPB), 9-cis retinoic acid (9-cis RA), CD33336, LG101093, and CD2781.

In one embodiment, a method of treating cancer or a proliferative disease in a patient in need thereof is provided, comprising administering an effective amount of at least one folate receptor inducer and also treating the patient with at least one compound according to formula X; wherein said folate receptor inducer upregulates folate receptor α. Preferably, said cancer or proliferative disease is selected from breast cancer, such as ER+ breast cancer, and ovarian cancer.

In one embodiment of the present invention, a method of treating cancer or a proliferative disease in a patient in need thereof is provided, comprising administering an effective amount of at least one folate receptor inducer and administering an effective amount of at least one compound according to formula X; wherein said folate receptor inducer upregulates folate receptor β. Preferably, said cancer or proliferative disease is selected from leukemia, and more preferably from acute myelogenous leukemia (AML) and chronic myelogenous leukemia (CML).

In a further embodiment, a method of treating cancer or a proliferative disease in a patient in need thereof is provided, comprising administering an effective amount of at least one folate receptor inducer, administering at least one histone deacetylase inhibitor, and treating the patient with an effective amount of at least one compound according to formula X. An example of a histone deacetylase inhibitor is trichostatin A (TSA). U.S. Patent Application Publication No. 2003/0170299 A1, WO 2004/082463, Kelly, K. M., B. G. Rowan, and M. Ratnam, Cancer Research 63, 2820-2828 (2003), Wang, Zheng, Behm, and Ratnam, Blood, 96:3529-3536 (2000).

The compounds of the present invention may form salts or solvates which are also within the scope of this invention. Reference to a compound of the formula (X) herein is understood to include reference to salts and solvates thereof, racemates, diastereomers, and enantiomers thereof, unless otherwise indicated. The term "salt(s)", as employed herein, denotes acidic and/or basic salts formed with inorganic and/or organic acids and bases. In addition, when a compound of formula (X) contains both a basic moiety, such as but not limited to a pyridinyl imidazolyl, amine or guanidinyl and an acidic moiety such as but not limited to a carboxylic acid, zwitterions may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula (X) may be formed, for example, by reacting a compound of formula (X) with an amount of acid or base, such as an equivalent amount, in a medium such as one in which the salt precipitates or in an aqueous medium followed by lyophilization.

The compounds of formula (X) that contain a basic moiety, such as but not limited to an amine, a guanidinyl group, or a pyridyl or imidazolyl ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula (X) that contain an acidic moiety, such as but not limited to a carboxylic acid, may form salts with a variety of organic and inorganic bases. Exemplary basic salts include ammonium salts; alkali metal salts such as sodium, lithiium, and potassium salts; alkaline earth metal salts such as calcium and magnesium salts; salts with organic bases (for example, organic amines) such as benzathines, dicyclohexylamines, hydrabamines (formed with N,N-bis (dehydroabietyl)ethylenediamine), N-methyl-D-glucamines, N-methyl-D-glycamides, t-butyl amines; and salts with amino acids such as arginine, lysine, and the like. Basic nitrogen-containing groups may be quaternized with agents such as lower alkyl halides (e.g. methyl, ethyl, propyl, and butyl chlorides, bromides, and iodides), dialkyl sulfates (e.g. dimethyl, diethyl, dibutyl, and diamyl sulfates), long chain halides (e.g. decyl, lauryl, myristyl, and stearyl chlorides, bromides, and iodides), aralkyl halides (e.g. benzyl and phenethyl bromides), and others.

Solvates of the compounds of the invention are also contemplated herein. Solvates of the compounds of formula (X) include, for example, hydrates.

All stereoisomers of the present compounds (for example, those which may exist due to asymmetric carbons on various substituents), including enantiomeric forms and diastereomeric forms, are contemplated within the scope of this invention. Thus, for example, each reference to compounds of Formula X, is intended to encompass compounds of Formula X'. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. Racemic forms can be resolved by physical methods, such as, for example, fractional crystallization, separation or crystallization of diastereomeric derivatives, or separation by chiral column chromatography. Individual optical isomers can be obtained from stereospecific processes, wherein starting materials and/or intermediates are selected having a stereochemistry corresponding with that desired for the end products, and the stereochemistry is maintained throughout the reactions, and/or the isomers can be obtained from racemates by any suitable method, including without limitation, conventional methods, such as, for example, salt formation with an optically active acid followed by crystallization.

All configurational isomers of the compounds of the present invention are contemplated, either in admixture, or in pure or substantially pure form. As can be appreciated, the preferred configuration can be a function of the particular compound and the activity desired. Configurational isomers may be prepared by the processes described herein, which may be stereoselective. In other words, a desired stereochemistry for the final compounds can be achieved by using starting materials having the corresponding desired stereochemistry, and then maintaining the stereoselectivity throughout the process of preparation. Alternatively, the compounds may be prepared as racemates or diastereomers, and then the desired stereochemistry may be achieved via separation of configurational isomers which can be achieved by any suitable method known in the field, e.g., such as column chromatography.

Throughout the specification, groups and substituents thereof may be chosen to provide stable moieties and compounds useful as pharmaceutically-acceptable compounds and/or intermediate compounds useful in making pharmaceutically-acceptable compounds. One skilled in the field will appreciate suitable selections for variables to achieve stable compounds.

Embodiments indicated herein as exemplary or preferred are intended to be illustrative and not limiting.

Other embodiments of the invention will be apparent to one skilled in the field such as, for example, considering combinations of the embodiments referenced above, and are contemplated as covered within the scope of the invention herein.

Utility

One of the proteins that is over-expressed or preferentially expressed in certain cancer cells is the folate receptor. Folic acid is required for DNA synthesis, and certain human tumor cells are known to over-express folate-binding proteins. For example, both Campbell et al., "Folate Binding Protein is a Marker for Ovarian Cancer," Cancer Research, Vol. 51 (Oct. 1, 1991), at pp. 5329-38, and Coney et al., "Cloning of a Tumor-Associated Antigen: MOv18 and MOv19 Antibodies Recognize Folate-binding Protein," Cancer Research, Vol. 51 (Nov. 15, 1991), at pp. 6125-31, report that folate-binding proteins are markers for ovarian cancer. Folate-receptor overexpression is also known for other cancers such as, for example, skin, renal, breast, lung, colon, nose, throat, mammary gland, and brain cancers, as well as other cancers referenced herein.

The compounds of the present invention are useful and can be delivered as epothilone-derived microtubule-stabilizing agents to tumors that express a folate receptor. They are useful in the treatment of a variety of cancers and other proliferative diseases, particularly those cancers characterized by cancer cells or tumors that express the folate receptor. The term "folate-receptor associated condition" as used herein comprises diseases or disorders characterized by expression of the folate receptor, or in other words, those diseases or disorders that can be diagnosed or treated based on the level of expression of the folate receptor in diseased tissue as compared with normal tissue. Compounds of the present invention are useful for forming conjugates. For example, compounds of the invention may be used to form the following conjugated compound of the formula I:

I

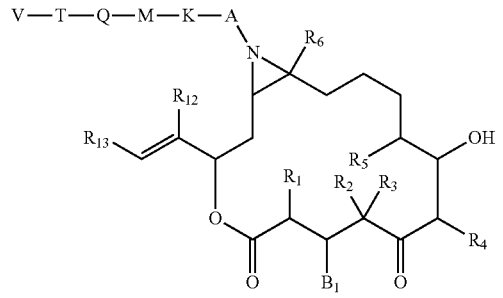

wherein:

V is folate, or an analog or derivative thereof;

Q is O, S, or $NR_7$;

M is a releasable linker;

K is O, S, or $NR_{7a}$;

A is $—(CR_8R_9)—(CH_2)_m$-Z- wherein Z is $—(CHR_{10})—$, —C(═O)—, —C(═O)—C(═O)—, —OC(═O)—, $—N(R_{11})C(═O)—$, $—SO_2—$, or $—N(R_{11})SO_2—$;

$B_1$ is hydroxyl or cyano and $R_1$ is hydrogen or $B_1$ and $R_1$ are taken together to form a double bond;

$R_2$, $R_3$, and $R_5$ are, independently, hydrogen, alkyl, substituted alkyl, aryl or substituted aryl; or $R_2$ and $R_3$ may be taken together with the carbon to which they are attached to form an optionally substituted cycloalkyl;

$R_4$ is hydrogen, alkyl, alkenyl, substituted alkyl, substituted alkenyl, aryl, or substituted aryl;

$R_6$ is hydrogen, alkyl or substituted alkyl;

$R_{7a}$, $R_7$, $R_8$, $R_9$, $R_{10}$, and $R_{11}$ are independently hydrogen, alkyl, substituted alkyl, cycloalkyl, substituted cycloalkyl, aryl, substituted aryl, heterocycloalkyl, substituted heterocycloalkyl, heteroaryl, or substituted heteroaryl;

$R_{12}$ is H, alkyl, substituted alkyl, or halogen;

$R_{13}$ is aryl, substituted aryl, heteroaryl or substituted heteroaryl;

m is 0 to 6;

T has the formula:

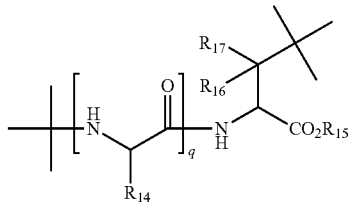

wherein $R_{14}$ at each occurrence is, independently, hydrogen, alkyl, substituted alkyl, aryl, substituted aryl, arylalkyl, substituted arylalkyl, cycloalkyl, substituted cycloalkyl, cycloalkylalkyl, substituted cycloalkylalkyl, heteroaryl, heteroarylalkyl, substituted heteroarylalkyl, substituted heteroaryl, heterocycloalkyl, or substituted heterocycloalkyl;

q is 1 to 10; and $R_{15}$, $R_{16}$ and $R_{17}$ are independently hydrogen, alkyl, substituted alkyl, or cycloalkyl.

As another nonlimiting example, compounds of the invention may be used to form the following conjugated compound of the formula Ia:

Ia

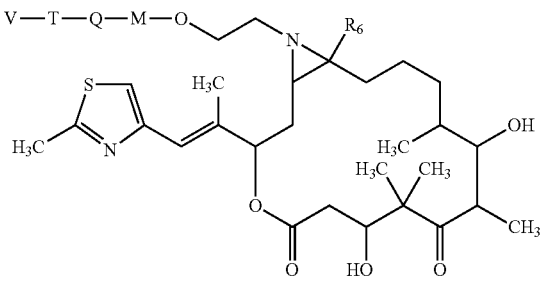

wherein V is a folate-receptor binding moiety. For example, V may have the following formula:

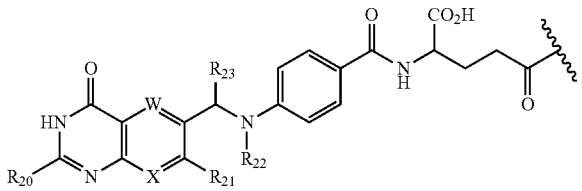

wherein W and X are independently CH or nitrogen;

$R_{20}$ is hydrogen, amino or lower alkyl;

$R_{21}$ is hydrogen, lower alkyl, or forms a cycloalkyl group with $R_{23}$;

$R_{22}$ is hydrogen, lower alkyl, lower alkenyl, or lower alkynyl; and $R_{23}$ is hydrogen or forms a cycloalkyl with $R_{21}$. Preferably, V is

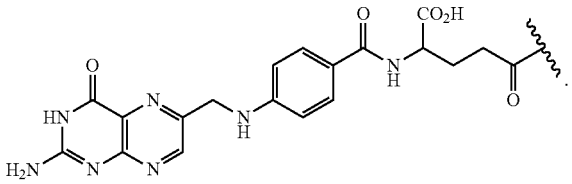

Compounds of the present invention can be conjugated to form compounds having the following Formula Ib:

Ib

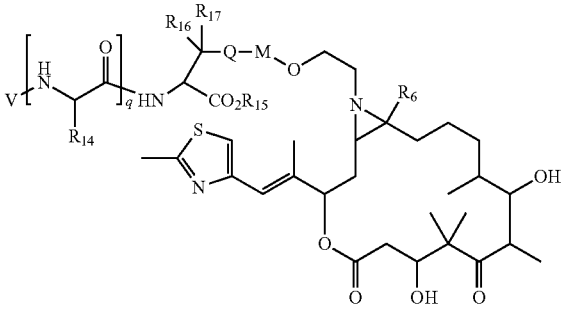

wherein

V is a folate-receptor binding moiety;

R is H or lower alkyl;

Q is O, S, or $NR_7$;

M is a releasable linker having the following formula:

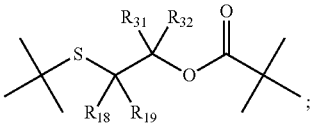

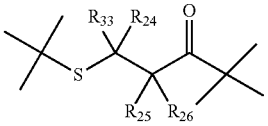

or

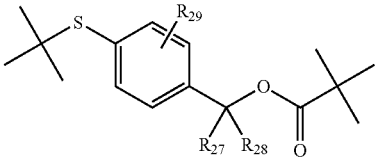

preferably

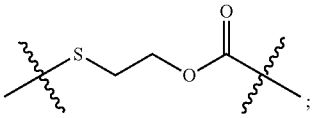

$R_{14}$ at each occurrence is, independently, hydrogen, alkyl, substituted alkyl, aryl, substituted aryl, arylalkyl, substituted arylalkyl, cycloalkyl, substituted cycloalkyl, cycloalkylalkyl, substituted cycloalkylalkyl, heteroaryl, heteroarylalkyl, substituted heteroarylalkyl, substituted heteroaryl, heterocycloalkyl, or substituted heterocycloalkyl; and is preferably a group selected from H, methyl, guanidinylpropyl, —$(CH_2)_{1-2}$—$CO_2H$, —$CH_2$—SH, —$CH_2$—OH, imidazolyl (methyl), aminobutyl, and —CH(OH)—$CH_3$; and is more preferably a $C_1$ to $C_3$ alkyl substituted with one of —C(═O)—OH or —NH—C(═NH)—$NH_2$;

q is 1 to 10; preferably 1 to 5;

$R_{15}$, $R_{16}$ and $R_{17}$ are independently hydrogen, lower alkyl or substituted lower alkyl; and $R_{18}$, $R_{19}$, $R_{31}$, $R_{32}$, $R_{33}$, $R_{24}$, $R_{25}$, $R_{26}$, $R_{27}$, $R_{28}$ and $R_{29}$ are each, independently, H, lower alkyl, substituted lower alkyl, cycloalkyl, or substituted cycloalkyl, or any of $R_{18}$ and $R_{19}$; $R_{31}$ and $R_{32}$; $R_{19}$ and $R_{31}$; $R_{33}$ and $R_{24}$; $R_{25}$ and $R_{26}$; $R_{24}$ and $R_{25}$; or $R_{27}$ and $R_{28}$ may be taken together to form a cycloalkyl.

Compounds of the present invention are especially useful for forming conjugated compounds, including pharmaceutically acceptable salts and solvates thereof, having the following formula:

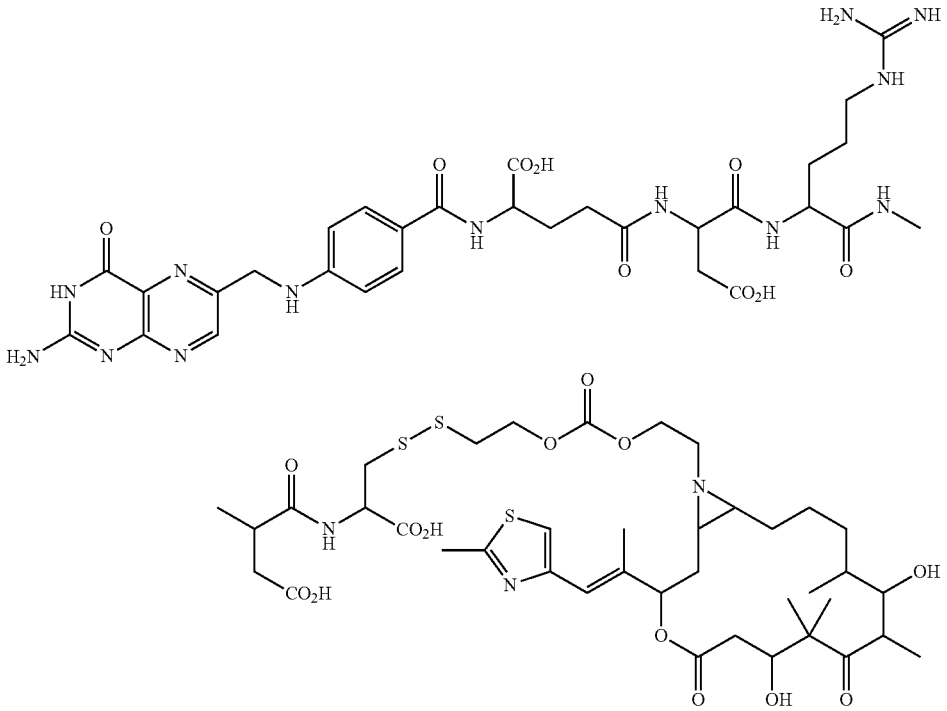

For any bivalent group listed herein, such as —$(CR_8R_9)$—$(CH_2)_m$-Z-, that is capable of insertion into compounds of Formula I,

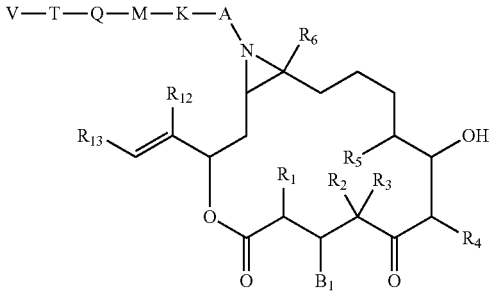

the insertion should be made from left to right. For example, in the following situation where A is defined as —$(CR_8R_9)$—$(CH_2)_m$-Z-, the methylene group is attached to K, and the Z group is attached to the nitrogen of the aziridinyl ring, as follows:

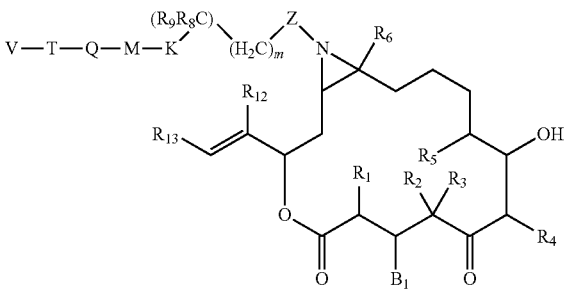

As a non-limiting example, such folate-receptor associated cancers include ovarian cancer and cancers of the skin, breast, lung, colon, nose, throat, mammary gland, liver, kidney, spleen, and/or brain; mesotheliomas, pituitary adenoma, cervical cancer, renal cell carcinoma or other renal cancer, choroid plexus carcinoma, and epithelial tumors (See, Asok, Antony, "Folate Receptors: Reflections on a Personal Odyssey and a Perspective on Unfolding Truth," Advanced Drug Delivery Reviews 56 (2004) at 1059-66).

Additionally, use of an antiestrogen (such as tamoxifen, ICI 182, 780), may be effective to increase the FR expression in certain cancer cells or tumor types to enhance the advantages obtained upon administering the compounds of the invention to patients, and/or to enhance the various diseases or tumor types that may be treated with the compounds according to the invention.

For example, the diseases that may be treated with the compounds of this invention, and/or upon a combination therapy comprising the compounds of this invention in combination with an antiestrogen, may further include, without limitation, the following

- carcinomas including those listed above and/or that of the bladder, pancreas, stomach, thyroid, and prostate;
- hematopoietic tumors of lymphoid lineage, including leukemias such as acute lymphocytic leukemia and acute lymphoblastic leukemia, and lymphomas, such as B-cell lymphoma, T-cell lymphoma, Hodgkins lymphoma, non-Hodgkins lymphoma, hairy cell lymphoma, and Burkitts lymphoma;
- hematopoietic tumors of myeloid lineage, including acute and chronic myelogenous leukemias and promyelocytic leukemia;
- tumors of the central and peripheral nervous system, including astrocytoma, neuroblastoma, glioma, and schwannomas;
- tumors of mesenchymal origin, including fibrosarcoma, rhabdomyosarcoma, and osteosarcoma; and other tumors, including melanoma, xeroderma pigmentosum, seminoma, keratoacanthoma, thyroid follicular cancer, and teratocarcinoma.

The compounds of the present invention are useful for treating patients who have been previously treated for cancer, as well as those who have not previously been treated for cancer. The methods and compositions of this invention can be used in first-line and second-line cancer treatments. Furthermore, the compounds of formula (X) may be useful for treating refractory or resistant cancers.

The compounds of the present invention may also be useful in treatment of other conditions responsive to microtubule-stabilizing agents delivered via the folate receptor, including but not limited to, arthritis, especially inflammatory arthritis and other inflammatory conditions mediated by activated macrophages, and central nervous system disorders such as Alzheimer's disease.

Furthermore, patients being treatment with the compounds of the present invention may receive a combination of treatments, for example, with other anti-cancer and cytotoxic agents or other treatments useful in the treatment of cancer or other proliferative diseases. In treating cancer, a combination of compounds of the instant invention and one or more additional agents and/or other treatments may be advantageous. The second agent may have the same or different mechanism of action than the compounds of formula (X). Especially useful are anti-cancer and cytotoxic drug combinations wherein the second drug chosen acts in a different manner or different phase of the cell cycle than the active drug moiety of the present compounds of the present invention.

Examples of classes of anti-cancer and cytotoxic agents include, but are not limited to, alkylating agents, such as nitrogen mustards, alkyl sulfonates, nitrosoureas, ethylenimines, and triazenes; antimetabolites, such as folate antagonists, purine analogues, and pyrimidine analogues; antibiotics or antibodies, such as monoclonal antibodies; enzymes; farnesyl-protein transferase inhibitors; hormonal agents, such as glucocorticoids, estrogens/antiestrogens, androgens/antiandrogens, progestins, and luteinizing hormone-releasing anatagonists; microtubule-disruptor agents, such as ecteinascidins or their analogs and derivatives; microtubule-stabilizing agents; plant-derived products, such as vinca alkaloids, epipodophyllotoxins, and taxanes; topoisomerase inhibitors; prenyl-protein transferase inhibitors; platinum coordination complexes; kinase inhibitors including multikinase inhibitors and/or inhibitors of Src kinase or Src/abl; signal transduction inhibitors; and other agents used as anticancer and cytotoxic agents such as biological response modifiers, growth factors, and immune modulators. The compounds of formula X may also be used in conjunction with radiation therapy.

Further examples of anticancer agents that may be used in combination with the compounds of the invention include Src kinase inhibitors, 'N-(2-Chloro-6-methylphenyl)-2-[[6-[4-(2-hydroxyethyl)-1-piperazinyl]-2-methyl-4-pyrimidinyl] amino]-5-thiazolecarboxamide, and other compounds described in U.S. Pat. No. 6,596,746 and U.S. patent application Ser. No. 11/051,208, filed Feb. 4, 2005, incorporated herein by reference; ixabepilone, an aza-epothilone B analog, and/or other epothilone analogs described in U.S. Pat. Nos. 6,605,599; 6,262,094; 6,288,237; 6,291,684; 6,359,140; 6,365,749; 6,380,395; 6,399,638; 6,498,257; 6,518,421; 6,576,651; 6,593,115; 6,613,912; 6,624,310, US Appl. Pub. No. 2003/0060623, published March 2003; German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253, WO 00/00485, US Pat. Appl. Pub. Nos. 2004/0053910 and 2004/0152708; cyclin dependent kinase inhibitors found in WO 99/24416 (see also U.S. Pat. No. 6,040,321); prenyl-protein transferase inhibitors found in WO 97/30992 and WO 98/54966; farnesyl protein transferase agents described in U.S. Pat. No. 6,011,029; CTLA-4 antibodies described in PCT publication no. WO01/14424, and/or a CTLA-4 antibody described in PCT publication no. WO 00/37504 such as, for example, the antibody known as CP-675206 (ticilimunab), or ORENCIA®; MDX-010; vinflunine (Javlor™), and Erbitux (cetuximab).

Other agents potentially useful in combination with compounds of the present invention may include paclitaxel (TAXOL®), docetaxel (TAXOTERE®) miscellaneous agents such as, hydroxyurea, procarbazine, mitotane, hexamethylmelamine, cisplatin and carboplatin; Avastin; and Herceptin.

The pharmaceutical compositions prepared according to the present invention can also be formulated or co-administered with other therapeutic agents that are selected for their particular usefulness in administering therapies associated with the aforementioned conditions. For example, the pharmaceutical compositions may be formulated with agents to prevent nausea, hypersensitivity and gastric irritation, such as antiemetics, and $H_1$ and $H_2$ antihistaminics.

The above other therapeutic agents, when employed in combination with the compounds of the present invention, can be used, for example, in those amounts indicated in the Physicians' Desk Reference (PDR) or as otherwise determined by one of ordinary skill in the art.

One embodiment of the invention comprises use of the present invention compounds in preparing pharmaceutical compositions for treatment of cancer, particularly for use in preparing pharmaceutical compositions for use in targeted drug delivery to tumors that overexpress or preferentially express the folate receptor. The pharmaceutical compositions of the present invention can be administered for any of the uses described herein by any suitable means, for example, parenterally, such as by subcutaneous, intravenous, intramuscular, or intrasternal injection or infusion techniques (e.g., as sterile injectable aqueous or non-aqueous solutions or suspensions), and/or in dosage unit formulations containing non-toxic, pharmaceutically acceptable vehicles or diluents. The pharmaceutical compositions can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution (0.9% Sodium Chloride Injection [Normal Saline] or 5% Dextrose Injection), or other suitable dispersing or wetting and suspending agents, including synthetic mono- or diglycerides, and fatty acids. Pharmaceutically acceptable compositions and/or methods of administering compounds of the invention may include use of cosolvents including, but not limited to ethanol, N,N dimethylacetamide, propylene glycol, glycerol and polyethylene glycols, e.g., polyethylene glycol 300 and/or polyethylene glycol 400, may comprise use of surfactants (pharmaceutically-acceptable surface active agent that may be used to increase a compound's spreading or wetting properties by reducing its surface tension), including without limitation, CREMOPHOR®, SOLUTOL HS15®, polysorbate 80, polysorbate 20, poloxamer, pyrrolidones such as N-alkylpyrrolidone (e.g., N-methylpyrrolidone) and/or polyvinylpyrrolidone; may also comprise use of one or more "buffers" (e.g., an ingredient which imparts an ability to resist change in the effective acidity or alkalinity of a medium upon the addition of increments of an acid or base), including, without limitation, sodium phosphate, sodium citrate, diethanolamine, triethanolamine, L-arginine, L-lysine, L-histidine, L-alanine, glycine, sodium carbonate, tromethamine (a/k/a tris[hydroxymethyl]aminomethane or Tris), and/or mixtures thereof.

The effective amount of the compound of the present invention can be determined by one of ordinary skill in the art, and includes exemplary dosage amounts for an adult human of from about 0.01-10 mg/kg of body weight of active compound per day, which can be administered in a single dose or in the form of individual divided doses, such as from 1 to 4 times per day. A preferred range includes a dosage of about 0.02 to 5 mg/kg of body weight, with a range of about 0.05-0.3, being most preferred. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to microtubule-stabilization associated conditions.

Compounds of the present invention, such as compounds disclosed in one or more of the following examples, have been tested in one or more of the assays described below and/or assays known in the field, and demonstrate a measurable level of activity as microtubule stabilizing agents.

Assays

Clonogenic Cell Survival Assay

Cancer cells were seeded at 3.0E+05 cells in a T75 flask with 10 ml of RPMI1640 media, free of folic acid, and containing 10% fetal bovine serum and 25 mM HEPES. Cells were grown in a 37° C. incubator containing 5% $CO_2$ for 2 days. On day 2, supernatants were removed from the flasks, and the flasks were divided into 2 groups. One group of cells were incubated with 5 ml of media containing 100 M of folic acid (Sigma) for 30 minutes and the others were grown in 5 ml of media without added folic acid. Cells were then treated with 20 nM of epothilone, epothilone analog, conjugated epothilone, or conjugated epothilone analog for one hour. At the end of the incubation, the drugs were removed from the flasks and the cells were washed with PBS buffer 3×. After washing, 5 ml of complete media were added into each flask, and the cell was grown in the $CO_2$ incubator for 23 hours. The next morning, the cells were removed from the flasks by trypsinization, cell numbers were determined, and then cells were plated in a 6 well plates. Ten days after plating, colonies were stained with crystal violet and counted. The surviving fractions were determined.

In Vitro MTS Proliferation/Cytotoxicity Assay

In vitro cytotoxicity was assessed in tumor cells using a tetrazolium-based colorimetric assay which takes advantage of the metabolic conversion of MTS (3-(4,5-dimethylthiazol-2-yl)-5-(3-carboxymethoxyphenyl)-2-(4-sulphenyl)-2H-tetrazolium, inner salt) to a reduced form that absorbs light at 492 nm. Cells were seeded 24 hr prior to addition of the epothilone, epothilone analog, conjugated epothilone, or conjugated epothilone analog. Following a 72 hour incubation at 37° C. with serially diluted compound, MTS, in combination with the electron coupling agent phenazine methosulfate, was added to the cells. The incubation was continued for 3 hours, then the absorbency of the medium at 492 nm was measured with a spectrophotometer to obtain the number of surviving cells relative to control populations. The results are expressed as median cytotoxic concentrations ($IC_{50}$ values).

Folate Receptor Assay

All sample preparation procedures used for the FR assay were performed at 4° C. Tissue samples were homogenized in homogenization buffer (10 mM Tris, pH 8.0, 0.02 mg/ml each of leupeptin and aprotinin; 1 ml buffer/50 mg tissue) using a PowerGen 125 homogenizer. Large debris was removed by mild centrifugation (3000×g for 15 min). Membrane pellets were then collected by centrifugation at 40,000×g for 60 min and resuspended in solubilization buffer (50 mM Tris, pH 7.4, 150 mM NaCl, 25 mM n-octyl-β-D-glucopyranoside, 5 mM EDTA, and 0.02% sodium azide). Insoluble material was removed by a second 40,000×g 60 min centrifugation, and the total protein concentration of the supernatants was determined by the bicinchoninic acid (BCA) method (Pierce Chemical). Each sample was then diluted to 0.25 mg/ml in solubilization buffer, and 100 μl was placed inside each of two Microcon-30 microconcentrators (30,000-MW cutoff, Millipore). Samples were then centrifuged at 14,000×g for 10 min at room temperature to pass all of the liquid through the membrane, as well as to retain the solubilized FRs on the surface of the microconcentrator's membrane. All subsequent centrifugation steps were performed using these same parameters. Then 55 μl of 30 mM acetate buffer (pH 3.0) was added to each microconcentrator, followed by a centrifugation step. Next, 55 μl of phosphate buffered saline (PBS) was dispensed into each microconcentrator, followed by another centrifugation. Then 50 μl of [$^3$H]folic acid binding reagent (120 nM [$^3$H]folic acid (Amersham) in 10 mM $Na_2PO_4$, 1.8 mM $KH_2PO_4$, pH 7.4, containing 500 mM NaCl, 2.7 mM KCl, and 25 mM n-octyl-β-D-glucopyranoside) or 50 μl of a competing reagent (binding reagent plus 120 μM unlabeled folic acid) was added to the appropriate concentrators. Following a 20-min incubation at room temperature, the concentrators were washed/centrifuged three times with 75 μl 50 mM n-octyl-β-D-glucopyranoside, 0.7 M NaCl in PBS, pH 7.4. After the final wash, the retentates containing the solubilized FRs were recovered from the membrane surface of the microconcentrators by two rinses with 100 μl of PBS containing 4% Triton X-100. The samples were then counted in a liquid scintillation counter (Packard Bioscience). Counts per minute (cpm) values were converted to picomoles of FR based on the cpm of a known standard, and the final results were normalized with respect to the sample protein content.

Animals and Tumors

Female CD2F1 mice (Harlan Sprague-Dawley Inc., 20-22 g) maintained in a controlled environment and provided with water and food ad libitum were used in these studies. The murine FRα(−) Madison 109 (M109) lung carcinoma (Marks et al., 1977) and the FR-expressing (FRα(+)) 98M109 variant were used to evaluate the efficacy of the epothilone, epothilone analog (e.g., epothilone derivative), folate-epothilone conjugate, or folate-epothilone analog conjugate. In addition, the human head and neck epidermoid carcinoma KB grown in nude mice was also used for this purpose.

Drug Treatment and Antitumor Efficacy Evaluation

For administration of epothilone or epothilone analogs to mice, an excipient consisting of the following was used: CREMOPHOR®/ethanol/water (1:1:8, v/v). The compounds were first dissolved in a mixture of CREMOPHOR®/ethanol (50:50). Final dilution to the required dosage strength was made less than 1 hr before drug administration. Mice were administered the agents by bolus IV injection through the tail vein. Folate-epothilone conjugates or folate-epothilone analog conjugates were prepared in sterile phosphate buffered saline and administered to mice by IV bolus injection through the tail vein at a volume of 0.01 mL/g of mice. Treatment of each animal was based on individual body weight.

The required number of animals needed to detect a meaningful response were pooled at the start of the experiment and each was given a subcutaneous inoculation of a tumor brei (2% w/v). Tumors were allowed to grow for 4 days. On the fourth day, animals were evenly distributed to various treatment and control groups. Treated animals were checked daily for treatment related toxicity/mortality. Each group of animals was weighed before the initiation of treatment (Wt1) and then again following the last treatment dose (Wt2). The difference in body weight (Wt2−Wt1) provides a measure of treatment-related toxicity.

Tumor response was determined by measurement of tumors with a caliper twice a week, until the tumors reached a predetermined "target" size of 1 gm. Tumor weights (mg) were estimated from the formula:

$$\text{Tumor weight}=(\text{length}\times\text{width}^2)\div 2$$

Antitumor activity was evaluated at the maximum tolerated dose (MTD) which is defined as the dose level immediately below which excessive toxicity (i.e. more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Tumor response end-point was expressed in terms of tumor growth delay (T-C value), defined as the difference in time (days) required for the treated tumors (T) to reach a predetermined target size compared to those of the control group (C).

To estimate tumor cell kill, the tumor volume doubling time (TVDT) was first calculated with the formula:

$$\text{TVDT}=\text{Median time (days) for control tumors to reach target size}-\text{Median time (days) for control tumors to reach half the target size}$$

And, $$\text{Log cell kill}=\text{T-C}\div(3.32\times\text{TVDT})$$

Statistical evaluations of data were performed using Gehan's generalized Wilcoxon test.

ABBREVIATIONS

The following abbreviations are used in the schemes and Examples herein for ease of reference:

CBZ-OSu=N-(Benzyloxycarbonyloxy)succinimide
DCM=dichloromethane
DEA=diethylamine
DIAD=diisopropyl azodicarboxylate
DIPEA=diisopropylethylamine
DMA=dimethylamine
DMF=dimethyl formamide
DMSO=dimethylsufoxide
EDC=1-(3-dimethylaminopropyl)-3-ethylcarbodiimide hydrochloride
EtOH=ethanol
EtOAc=ethyl acetate
FR=folate receptor
HOBt=n-hydroxy benzotriazole
HPCL=high performance liquid chromatography
iPr—OH or IPA=isopropyl alcohol
LC/MS=liquid chromatography/mass spec
LDA=lithium diisopropylamide
MeOH=methanol
OTES=o-triethylsilyl;
OMs=mesylate;
Ph=phenyl
Pd/C=palladium on carbon
PyBOP=benzotriazol-1-yl-oxytripyrrolidinophosphonium hexafluorophosphate
Py=pyridyl
RT=room temperature
Sat'd=saturated
THF=tetrahydrofuran
TFA=trifluoroacetic acid
TLC=thin layer chromatography
TESCL=chlorotriethylsilane
UV=ultraviolet.

Methods of Preparation

Compounds of the present invention may generally be prepared according to the following schemes and the knowledge of one skilled in the art, and/or using methods set forth in U.S. Pat. Nos. 6,605,599; 6,831,090; 6,800,653; 6,291,684; 6,719,540; 7,172,884, US Pat. Appl. Pub. No. 2005/0002942 and Organic Letters, 2001, 3, 2693-2696, the disclosures of which are herein incorporated by reference and/or in the Examples that follow.

As shown in Scheme 1, a compound of formula X can be prepared from a compound of formula II. Compounds of formula II can be obtained by fermentation (see, e.g. Gerth et al., "Studies on the Biosynthesis of Epothilones: The Biosynthetic Origin of the Carbon Skeleton," Journal of Antibiotics, Vol. 53, No. 12 (December 2000), and Hofle et al., "Epothilone A and B-Novel 16-Membered Macrolides: Isolation, Crystal Structure, and Conformation in Solution", Angew. Chem. Int. Ed. Engl., Vol. 35, No. 13/14, 1567-1569 (1996), the disclosures of which are herein incorporated by reference) or by synthesis (see, e.g. Vite et al. U.S. Pat. Nos. 6,605,599; 6,242,469; 6,867,333 and US Pat. Appl. Pub. 2006/004065, and Johnson et al. Organic Letters, 2000, 2:1537-1540) the disclosures of which are herein incorporated by reference in their entirety). For example a compound of formula II where $R_2$, $R_3$, $R_4$, $R_5$, and $R_{12}$ are methyl, $B_1$ is hydroxyl, $R_1$ and $R_6$ are hydrogen, and $R_2$ is 2-methylthiazol-4-yl is referred to as epothilone A and can be obtained from fermentation of Sorangium cellulosum as referenced above. A compound of formula II can be converted to a compound of formula III where P is a silyl protecting group such as triethylsilyl, t-butyldimethylsilyl, t-butyldiphenylsilyl, triisopropylsilyl, and the like (see, e.g., Greene et al., "Protective groups in Organic Synthesis", John Wiley and Sons, Inc.). For example, a compound of formula III where P is triethylsilyl can be prepared by treatment of a compound of formula II with chlorotriethylsilane in the presence of Hunig's base. In the case where $B_1$ is hydroxyl in the compound of formula II, then $B_1$ would also be converted to the corresponding silyl ether. A halohydrin of formula IV (Y is Cl, Br, or I) can be prepared from a compound of formula III by treatment with a metal halide salt by methods known in the art. For example, epoxide opening using magnesium bromide etherate at low temperature (−20 to −5° C.) can provide diastereomeric halohydrins, where Y is bromine. A compound of formula V can be prepared from a compound of formula IV by displacement of the halogen using, for example, sodium azide in a polar solvent such as dimethylformamide. An ordinarily skilled artisan will recognize that the stereochemistry at $C_{12}$ as depicted in Scheme I should not be construed as limiting, but rather exemplary. If desired, inversion of the stereochemistry at the $C_{12}$ position can be achieved following the Mitsunobu protocol which is well established in the art. For example, treatment of a compound of formula V with p-nitrobenzoic acid, diethylazodicarboxylate, and triphenylphosphine provides the corresponding nitrobenzoate ester, which can then be cleaved by mild ester hydrolysis using, for example, methanolic solutions of ammonia to provide a compound of formula VI. Again, the stereochemistry for $C_{12}$ as depicted for compound VI is not limiting, and is depicted as such to show that treatment of compound V as described will invert the stereochemistry at that position. Alternatively, other organic acids, azodicarboxylates, and organophosphines can be used to effect the Mitsonuobu inversion. A compound of formula VII where OG is a leaving group such as mesylate, tosylate, nosylate, triflate and the like can be prepared from a compound of formula VI by methods known in the art. For example, treatment of VI with methanesulfonyl chloride and triethylamine in a suitable organic solvent such as dichloromethane provides a compound of formula VII where OG is mesylate. A compound of formula VIII can be prepared from a compound of formula VII by reduction of the azido group with a reducing agent such as an organophosphine (e.g., trimethylphosphine). Alternatively, a compound of formula VIII can be prepared directly from a compound of formula VI using an organophosphine reducing agent such as triphenylphosphine. A compound of formula IX can be prepared from a compound of formula VIII by methods known in the art (see, e.g., U.S. Pat. No. 6,800,653; and Regueiro-Ren et al., Organic Letters, 2001, 3, 2693-2696). For instance, a compound of formula IX where H—K-A- is 2-hydroxyethyl can be prepared from a compound of formula VIII by alkylation of the aziridine ring using, for example, excess 2-bromoethanol and a base such as potassium carbonate. A compound of formula X can be prepared from a compound of formula IX by removal of the silyl ether protecting groups using methods known in the art (see, e.g., Greene et al., "Protective groups in Organic Synthesis", John Wiley and Sons, Inc.). For instance, when P is triethylsilyl, treatment of a compound of formula IX with trifluoroacetic acid in dichloromethane effects deprotection to provide a compound of formula X.

SCHEME 1

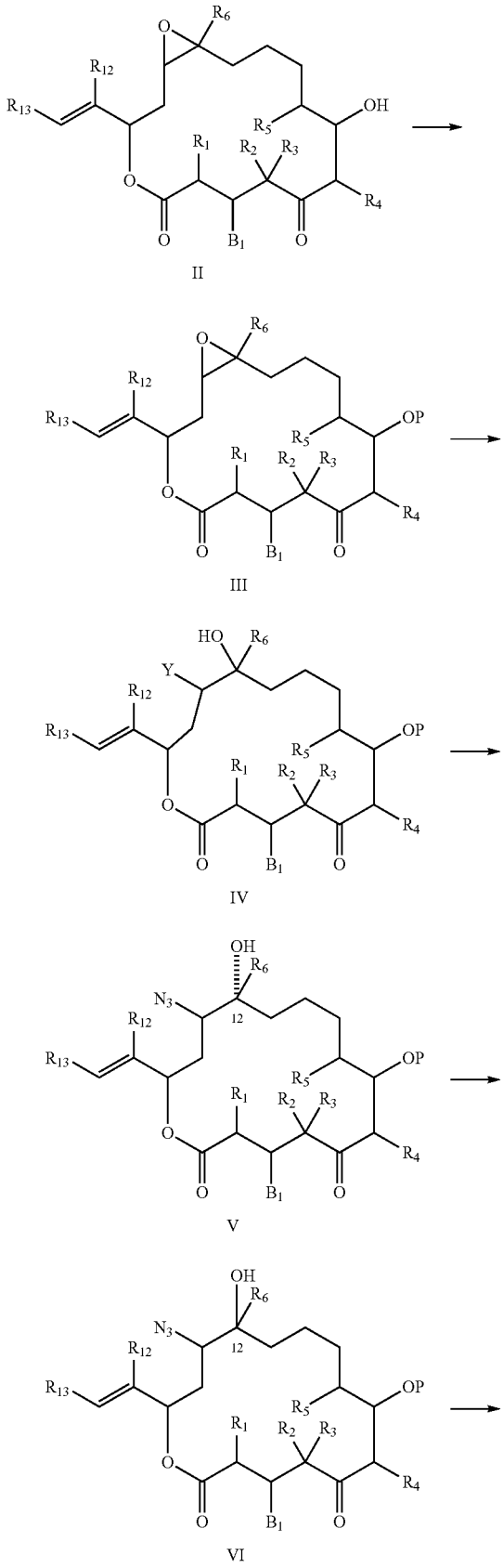

-continued

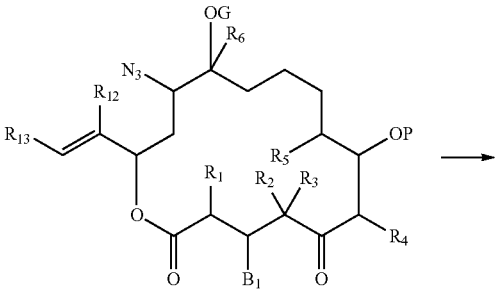

VII

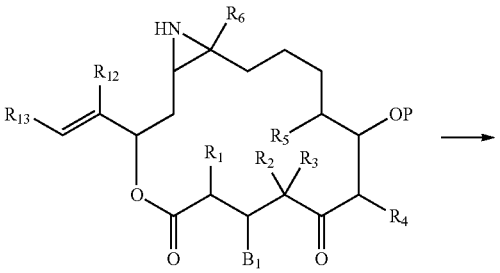

VIII

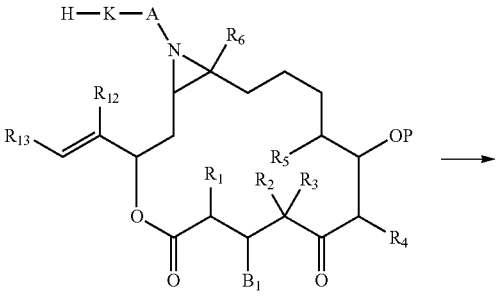

IX

-continued

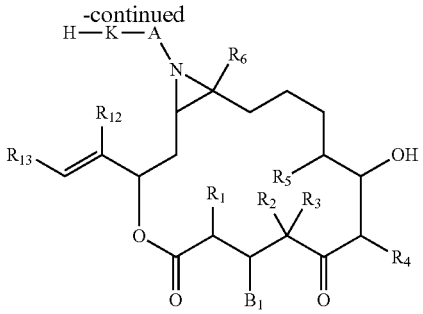

X

Scheme 2 shows a process for making a folate analog or derivative V and bivalent linker T-Q having the formula XI, below, that may be used with compounds of the invention to make conjugated molecules for targeted drug delivery, e.g., as per formula I, previously described. As shown in Scheme 2, a folate analog and bivalent linker can be assembled using methods known in the art, especially in the case where V is folic acid or a folic acid analog, as described, for example, by Jackson, et al., Advanced Drug Delivery Rev. 56 (2004) 1111-1125, the disclosure of which is herein incorporated by reference, and T-Q is a peptide. For example, peptidyl folate XI can be prepared as shown in Scheme 2. Sequential peptide coupling of a cysteine-loaded polystyrene resin with Fmoc-protected aspartate, arginine, aspartate, and then glutamate can be effected using PyBOP as coupling agent and piperidine as Fmoc-deprotection agent. $N^{10}$-Trifluoroacetamide-protected pteroic acid can be prepared in two steps by enzymatic (carboxypeptidase G) conversion of folic acid to pteroic acid, followed by $N^{10}$-protection using trifluoroacetic anhydride. Next, coupling of the $N^{10}$-protected pteroic acid to the resin-bound peptide followed by cleavage from the resin with trifluoroacetic acid and removal of the $N^{10}$-trifluoroacetyl group using ammonium hydroxide provides a V-T-Q fragment of a compound of formula I where V is folic acid and T-Q is -Asp-Arg-Asp-Cys-OH. Alternatively, pteroic acid analogs could be used in place of pteroic acid and other amino acids, could be used in place of those illustrated in Scheme 2.

Scheme 2

H-Cys(4-methoxytrityl)-2-chlorotrityl-Resin
(loading 0.57 mmol/g)

1) Fmoc-Asp(OtBu)-OH, PyBOP, DIPEA, DMF then piperidine
2) Fmoc-Arg(Pbf)-OH, PyBOP, DIPEA, DMF then piperidine
3) Fmoc-Asp(OtBu)-OH, PyBOP, DIPEA, DMF then piperidine
4) Fmoc-Glu-OtBu, PyBOP, DIPEA, DMF then piperidine
5) $N^{10}$TFA, 2.5% $H_2O$, 2.5% i-$Pr_3SiH$,
6) 92.5% TFA, 2.5% $H_2O$, 2.5% i-$Pr_3SiH$, and 2.5% ethanedithiol
7) $NH_4OH$ aq., then HCl aq.

-continued

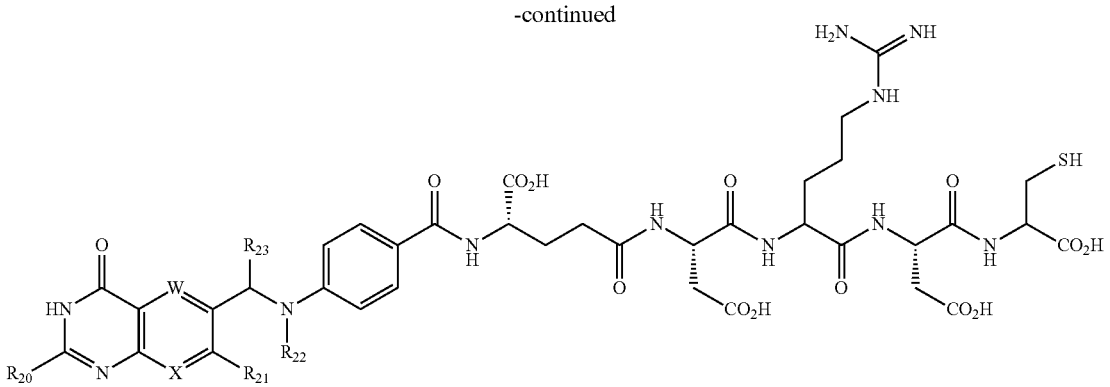

XI

Scheme 3, below, shows a method for using the epothilone derivatives of the present invention to prepare a conjugated molecule of formula I, for use in targeted drug delivery. As shown in Scheme 3, assembly of compounds of formula I can be achieved by coupling compounds of formula X to a fragment V-T-Q by stepwise incorporation of a releasable linker M. By way of illustration, a compound of formula X where -A-K—H is —$CH_2CH_2OH$ can be converted to a disulfanylethyl carbonate XIII using an activated benzotriazole compound of formula XII. A compound of formula XII can be prepared from mercaptoethanol, methoxycarbonyl sulfenyl chloride, and an optionally substituted 2-mercaptopyridine to provide an intermediate 2-(2-pyridin-2-yl) disulfanyl)ethanol, which can then be converted to a compound of formula XII by treatment with diphosgene and an optionally substituted 1-hydroxybenzotriazole. Subsequent disulfide exchange with a peptidyl folate such as XI provides a compound of formula I where V is folic acid, T-Q is a -Asp-Arg-Asp-Cys-OH, M is —$SCH_2CH_2O(C{=}O)$—, A is —$CH_2CH_2$— and K is O,

SCHEME 3

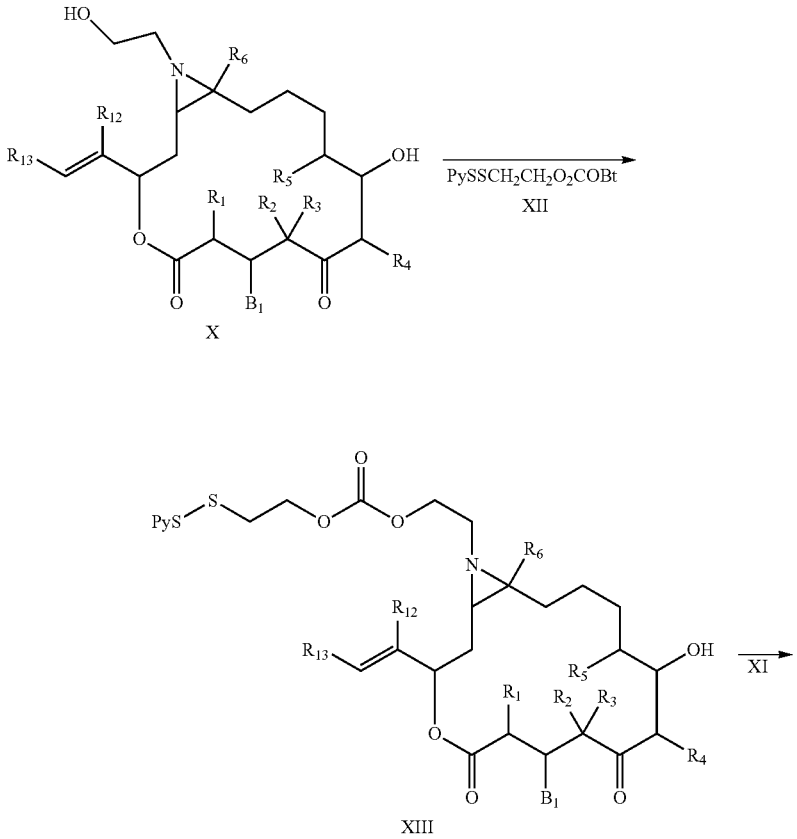

X

XIII

-continued

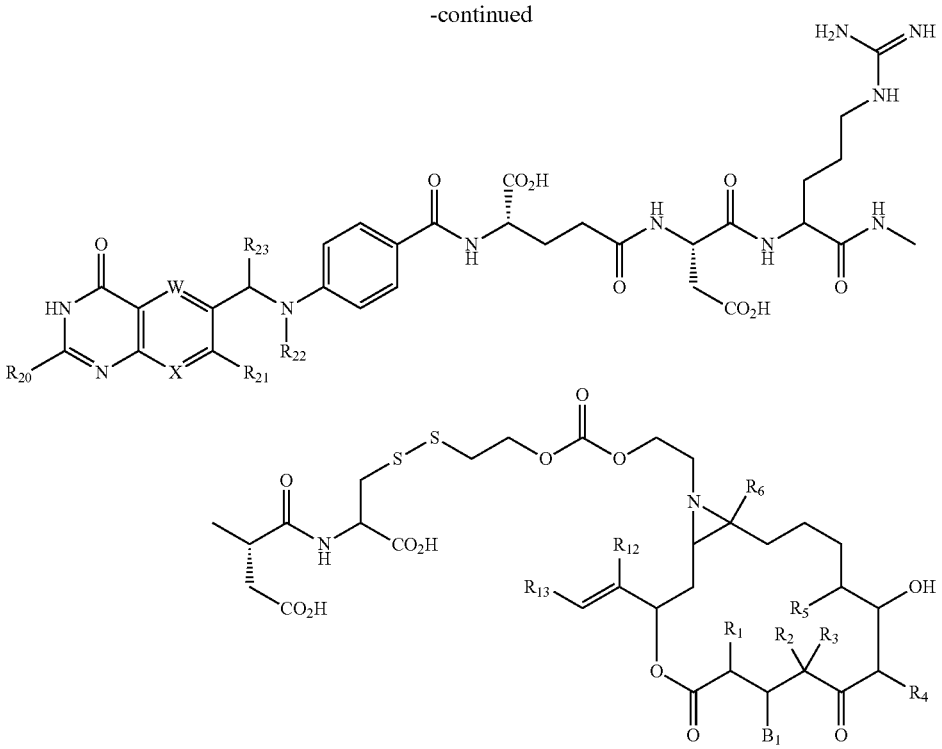

I

Scheme 4 illustrates an alternative method for making a compound of formula X from a compound of formula XIV (see, U.S. patent application Ser. No. 60/940,088, filed May 25, 2006, incorporated herein in its entirety by reference). Compounds of formula XIV can be obtained by methods well known in the field, for example, by fermentation (see, e.g. Gerth et al., "Studies on the Biosynthesis of Epothilones: The Biosynthetic Origin of the Carbon Skeleton," Journal of Antibiotics, Vol. 53, No. 12 (December 2000), and Hofle et al., "Epothilone A and B-Novel 16-Membered Macrolides: Isolation, Crystal Structure, and Conformation in Solution", Angew. Chem. Int. Ed. Engl., Vol. 35, No. 13/14, 1567-1569 (1996), the disclosures of which are herein incorporated by reference) or by total synthesis (see, e.g. Vite et al. U.S. Pat. Nos. 6,605,599; 6,242,469; 6,867,333 and US Pat. Appl. Pub. 2006/004065, the disclosures of which are herein incorporated by reference in their entirety). For example a compound of formula XIV where $R_2$, $R_3$, $R_4$, $R_5$, and $R_{12}$ are methyl, $B_1$ is hydroxyl, $R_1$ and $R_6$ are hydrogen, and $R_2$ is 2-methylthiazol-4-yl is referred to as epothilone C and can be obtained from fermentation of Sorangium cellulosum as referenced above. A compound of formula XIV can be converted to a compound of formula XV where P is a silyl protecting group such as triethylsilyl, t-butyldimethylsilyl, t-butyldiphenylsilyl, triisopropylsilyl, and the like (see, e.g., Greene et al., "Protective groups in Organic Synthesis", John Wiley and Sons, Inc.). For example, a compound of formula XV where P is triethylsilyl can be prepared by treatment of a compound of formula XIV with chlorotriethylsilane in the presence of base such as Hunig's base. In the case where $B_1$ is hydroxyl in the compound of formula XIV, then $B_1$ would also be converted to the corresponding silyl ether. A halohydrin of formula XVI or XVII (Y is Cl, Br, or I) can be prepared from a compound of formula XV by treatment with a halogenating agent such as $Y_2$. For example, electrophilic addition in polar solvents such as acetonitrile using iodine can stereoselectively provide regioisomeric halohydrins of formulas XVI and XVII, where Y is iodine. Alternatively N-halo succinimides can also be used for the same transformation. A compound of formula XVIII can be prepared from compounds of formulas XVI and/or XVII by epoxide ring closure in the presence of bases such as triethylamine or Hunig's base in a polar/aqueous solvent system such as acetonitrile/water. If desired, compound XIV can be directly transformed into a compounds of formula XVI and/or XVII (where P is H), which could then be converted into the epoxide XVIII (where P is H). A compound of formula XVIII can be transformed into the azido-alcohols of formulas VI and XIX by azide displacement in the presence of inorganic azide salts or tetraalkyl ammonium azides in alcoholic solvents. In the case where P is a silyl protecting group, compounds of formulas XX and/or XXI where OG is a leaving group such as mesylate, tosylate, nosylate, trifiate and the like can be prepared from compounds of formulas VI and/or XIX by methods known in the art. For example, treatment of VI and/or XIX with methanesulfonyl chloride and triethylamine in a suitable organic solvent such as dichloromethane provides compounds of formulas XX and XXI where OG is mesylate. A compound of formula VIII can be prepared from compounds of formulas XX and/or XXI by reduction of the azido group through methods known in the art. For example, compound VIII can be prepared from compounds of formulas XX and/or XXI through reaction with a reducing agent such as an organophosphine (e.g., trimethylphosphine) in polar solvents such as acetonitrile. Alternatively, when P is H, compound of formula VIII can be directly prepared from compounds of formulas VI and/or XIX by reduction of the azido group with a reducing agent such as an organophosphine (e.g., triphenylphosphine) in polar solvents such as acetonitrile. A compound of formula IX can be prepared from a compound of formula VIII by methods known in the art (see, e.g., U.S. Pat. No. 6,800,653; and Regueiro-Ren et al., Organic Letters, 2001, 3, 2693-2696). For instance, a compound of formula IX where H—K-A- is 2-hydroxyethyl can be prepared from a compound of formula VIII by alkylation of the aziridine ring using, for example, excess 2-bromoethanol and a base such as potassium carbonate. In case P is a trialkylsilyl, a compound of formula X can be prepared from a compound of formula IX by removal of the silyl ether protecting groups using methods known in the art (see, e.g., Greene et al., "Protective groups in Organic Synthesis", John Wiley and Sons, Inc.). For instance, when P is triethylsilyl, treatment of a compound of formula IX with trifluoroacetic acid in dichloromethane effects deprotection to provide a compound of formula X.

SCHEME 4

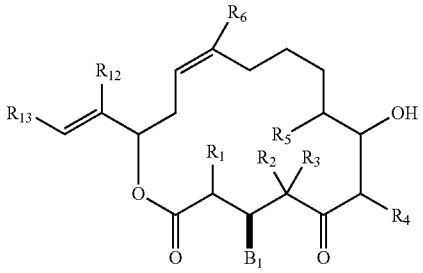

XIV

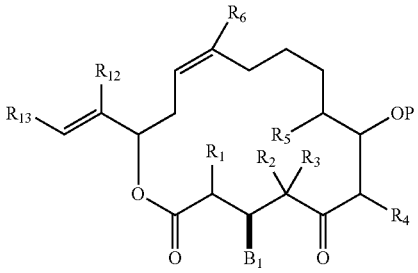

XV

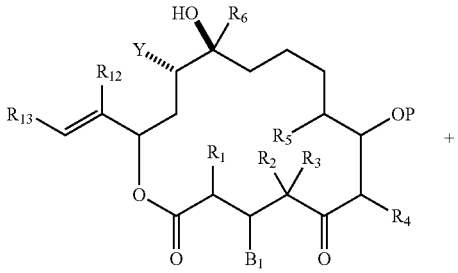

XVI

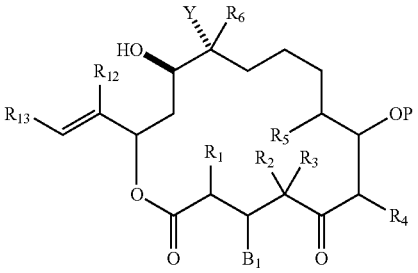

XVII

-continued

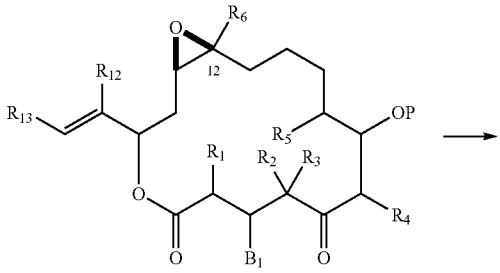

XVIII

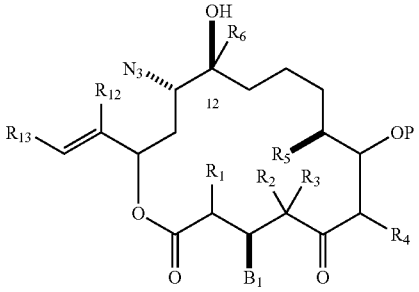

VI

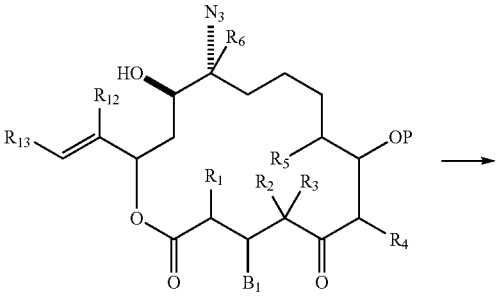

XIX

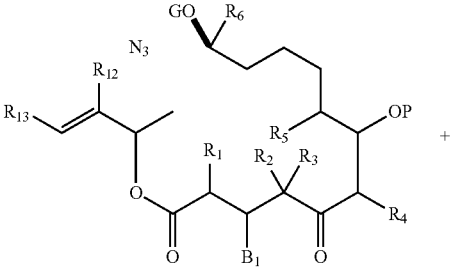

XX

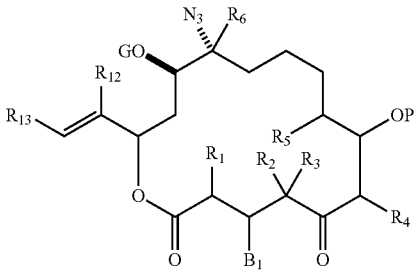

XXI

-continued

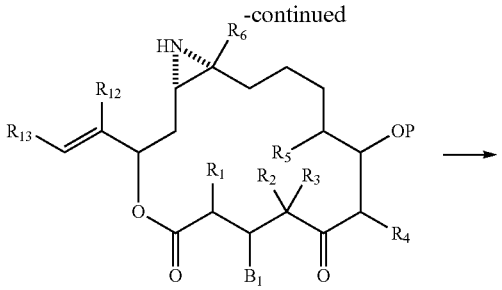

VIII

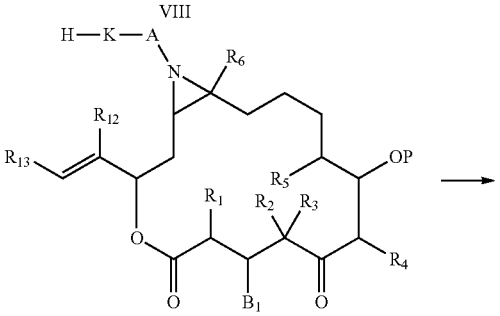

IX

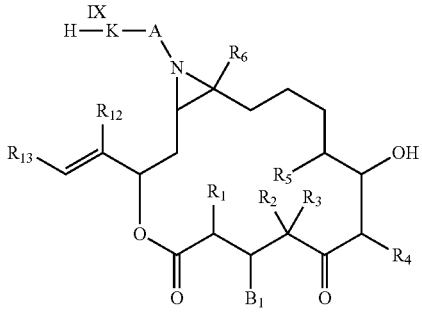

X

The invention will now be further described with reference to the following illustrative examples.

EXAMPLES

Example 1

Folate Conjugated Epothilone Analogs

As described in the detailed description above, analogs and derivatives of folate are described in Vlahov. In research and development directed toward folate receptor targeting to tumor cells of conjugated epothilone and epothilone analog compounds, several compounds were conjugated to folate. For example, Compound AA and Compound BB were considered as candidates for conjugation to folic acid:

Compound AA

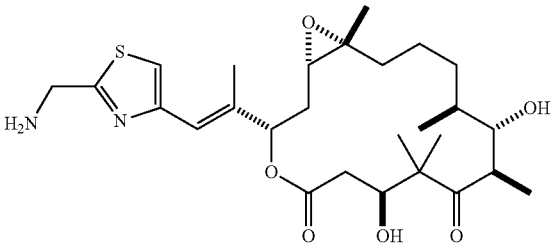

-continued

Compound BB

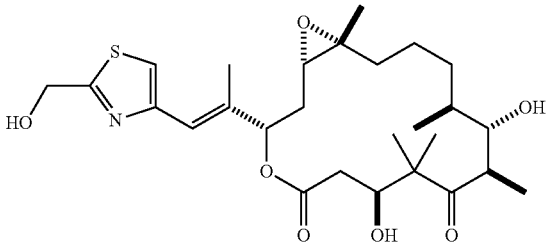

Compound AA has activity in Phase II clinical trials, and six folate conjugates of Compound AA (Compounds AA.I to AA.VI; see FIG. 1) were prepared and optionally tested for chemical stability, FR binding, and FR-mediated activity in cell culture.

The binding of these folate conjugates of Compound AA to FR was determined in an assay that measures displacement of radiolabeled folic acid from FR expressed on KB tumor cells grown to confluence. Finding of the folate conjugates of Compounds AA.I and AA.II to FR was deemed acceptable [relative affinity (RA)>0.25; RA of folic acid=1.0]. However, surprisingly, none of the six conjugates of Compound AA shown in FIG. 1 displayed appreciable cytotoxicity against KB tumor cells in antiproliferation assays that measure $^3$H-thymidine incorporation (data not shown).

Since conjugates of Compound AA demonstrated disappointing cytotoxicity against tumor cells, studies were conducted using three conjugates of Compound BB (Compounds BB.I to BB.III). Compound BB is also known as epothilone F, and is an analog of Compound AA, where the 21-amino group is replaced by a 21-hydroxyl group. While Compound BB.II (FIG. 2) displayed cytotoxicity at high concentrations, the activity was not attenuated in competition studies using excess of folic acid. Therefore, the observed cytotoxicity was attributed to non-specific release of Compound BB.II.

Other epothilone analogs, e.g., aziridinyl epothilones, are known in the art (see, e.g., U.S. Pat. No. 6,399,638; Regueiro-Ren, A, et al. (2001) Org. Letters. 3:2693-96) and show potent antitumor cytotoxicity. For example, an MTS assay that compared the relative cytotoxic potency of a number of epothilone analogs against a pair of taxane-resistant cancer cell lines (HCTVM46 and A2790Tax) was conducted (see Table 1). HCTVM46 is a human colon carcinoma cell line derived from the sensitive HCT116 parent line, and is resistant to taxanes due to overexpression of the 170 kD p-glyprotein drug efflux transporter. A2780Tax is a human ovarian carcinoma cell line derived from the parent A2780 line, and is resistant to paclitaxel as a result of a mutation in the tubulin amino acid sequence that impairs the ability of paclitaxel to bind.

As is shown in Table 1, various aziridinyl epothilone analogs (Compounds CC-EE) show potent antitumor activity against both the HCT116 colon and A2780 ovarian carcinoma cell lines, compared to other known antitumor agents, e.g., paclitaxel, compound AA, and epothilone B.

TABLE 1

In vitro activity of 12,13-aziridinyl epothilones

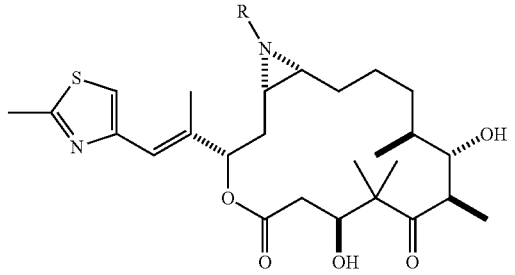

| Compound | R | HCT116 $IC_{50}$ (nM)[1] | R/S Ratio[2] | A2780 $IC_5$ (nM)[1] | R/S Ratio[3] |
|---|---|---|---|---|---|
| CC | —H | 4.2 ± 2.8 | 3.1 | 3.4 ± 1.5 | 4.7 |
| DD | —$CH_3$ | 0.37 ± 0.13 | 0.6 | 0.25 ± 0.06 | 4.1 |
| EE | —$CH_2CH_2OCH_3$ | 0.40 ± 0.25 | 0.8 | 0.22 ± 0.12 | 4.7 |
| paclitaxel | — | 3.3 ± 1.0 | 150 | 3.1 ± 1.0 | 22.1 |
| AA | — | 1.2 ± 0.3 | 14.8 | 1.1 ± 0.4 | 3 |
| Epothilone B | — | 0.40 ± 0.13 | 0.5 | 0.23 ± 0.09 | 2.5 |

[1]Mean $IC_{50}$ ± SD calculated from four separate experiments.

[2]R/S ratio = HCT116 $IC_{50}$/HCT116VM46 $IC_{50}$

[3]R/S ratio = A2780 $IC_{50}$/A2780Tax $IC_{50}$

Despite the antitumor activities of aziridinyl epothilone compounds CC-EE, the only hydroxyl groups on these molecules available for conjugation to folate are those found at the $C_3$ and $C_7$ carbon atoms. Consequently, having researched a number of epothilone compounds and analogs, there remained a challenge to discover a compound that would be readily available for conjugation to folate, and which would demonstrate activity via specific release of the active epothilone moiety in the tumor cells.

The aziridinyl epothilone compound G was discovered, having the formula,

Compound G

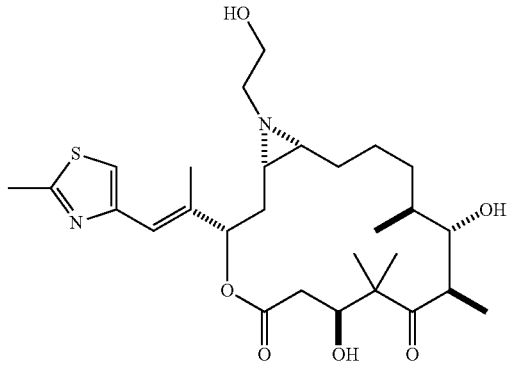

Compound G (see Examples 2 and 3) proved surprisingly easy to conjugate to folic acid to form Compound J (see Example 2) with relative affinity of 0.77 for folate receptor, when compared to folic acid.

Unexpectedly, the polar hydroxyl group on the aziridine side chain did not adversely affect the antitumor activity of the aziridine epothilone analogs. This is important because it is the aziridine epothilone analog, e.g., Compound G, that mediates the antitumor effects upon release from folic acid. The potency of Compound G, and three other highly potent epothilone analogs (ixabepilone, Compound AA, and Compound BB) were evaluated by the colony formation assay that is described above. The concentration needed to kill 90% of clonogenic KB cancer cells ($IC_{90}$) was determined after a drug exposure duration of 17 hours. As shown in FIG. 3, compound G exhibited an $IC_{90}$ of 4.3 nM and was ~2, 4, and 6-fold more potent than compound CC, compound AA, and ixabepilone, respectively.

Conjugation of compound G to form Compound J did not affect the antitumor activity of compound G. Compound J demonstrated substantial cytotoxic activity against tumor cells in vivo. In the KB in vivo FRα(+) tumor model, compound J demonstrated activity both at is maximum tolerated dose (MTD) and at two lower does levels that produced minimal toxicity (see FIG. 4). In contrast, ixabepilone was active only at its MTD (5 μmol/kg). When compared at the MTDs, compound J produced superior antitumor effects than ixabepilone (FIG. 4).

Compound J

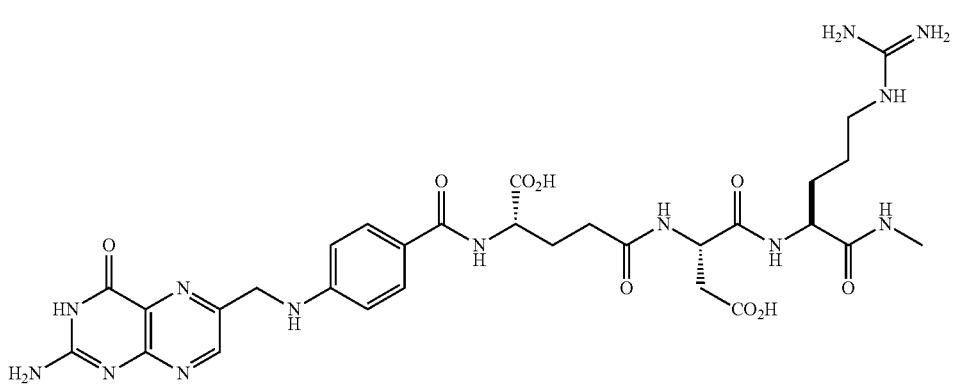

-continued

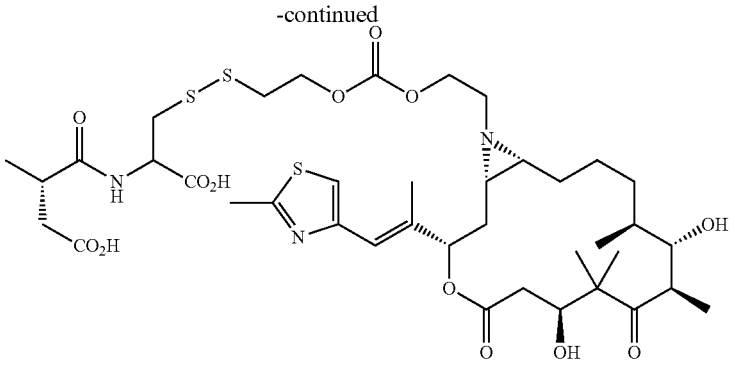

Figure 5:
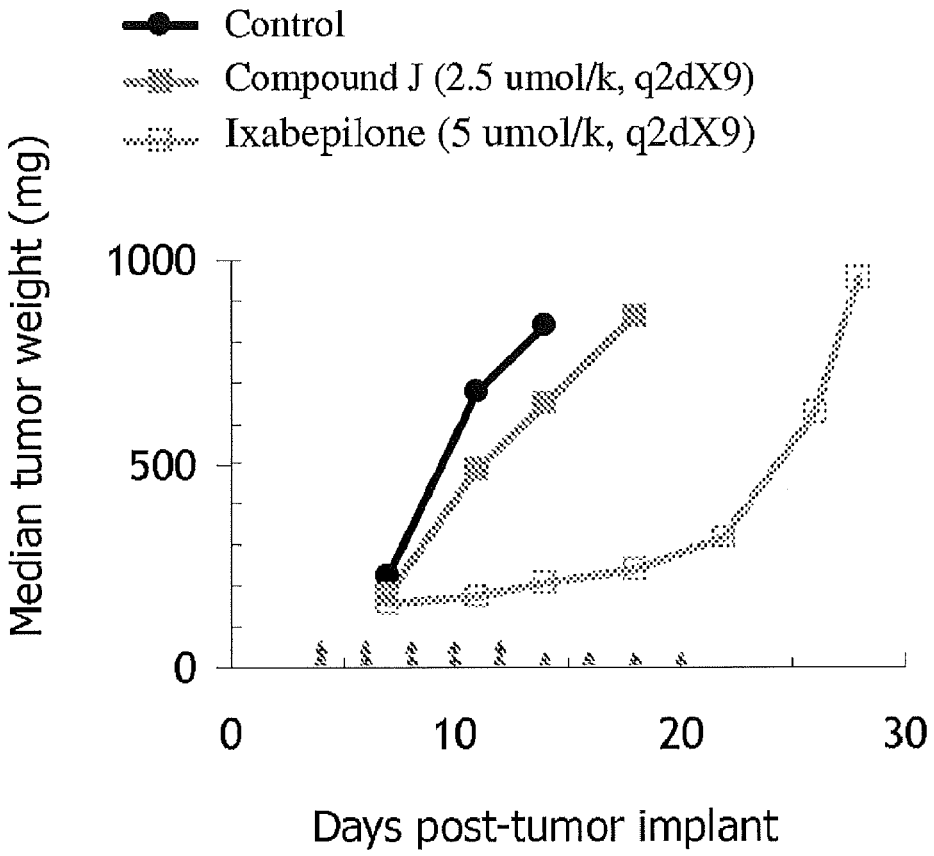
FIG. 5 demonstrates the in vivo antitumor effects of Compound J (grey squares) or ixabepilone (white squares), compared to no treatment (control; black circles), against FR (−) M109 murine lung carcinoma as a measure of median tumor weight (mg; y-axis) several days post tumor implant (x-axis).

In contrast, with the FRα(−) M109 parent tumor model, Compound J had poor activity at all dose levels tested, including at its MTD (2.4 μmol/kg), whereas ixabepilone was active at its MTD of 5 μmol/kg. (FIG. 5). These results indicate that the FRα(−) M109 is sensitive to ixabepilone and the inactivity of compound J is likely largely a consequence of the absence of FRα expression by this tumor. These results also provide evidence that the antitumor activity of compound J may be mediated through the FRα receptors.

Figure 6:
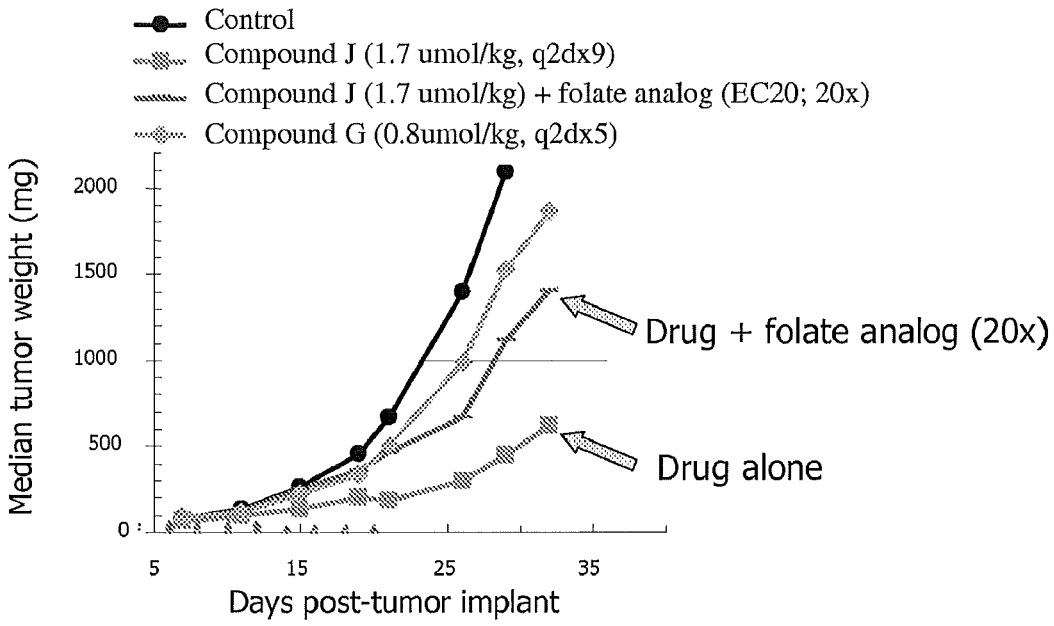
FIG. 6 demonstrates the in vivo antitumor effects, as a measure of median tumor weight (mg; y-axis) several days post tumor implant (x-axis), of no treatment (control, black circles), treatment with Compound J alone (grey squares), Compound J in the presence of a folate analog, black bars), or treatment with Compound G (grey diamonds).

Further evidence of the FRα mediated drug delivery mechanism of compound J is provided by the observation that co-administration of a folate analog at 20-fold excess of the dose of compound J could substantially compete with compound J for receptor binding and protect FRα(+) 98M109 tumors from the antitumor effects of compound J. (FIG. 6). Since Compound G and the conjugate (Compound J) have surprising anti-tumor effects both in vitro and in vivo, and since the antitumor activities of Compound J may be attributed to FRα(+)-mediated effects, also described herein is the conjugation of aziridinyl epothilone analog Compound G (see Examples 2 and 3) to form Compound J. (See Example 2).

Example 2

Preparation of Compound J

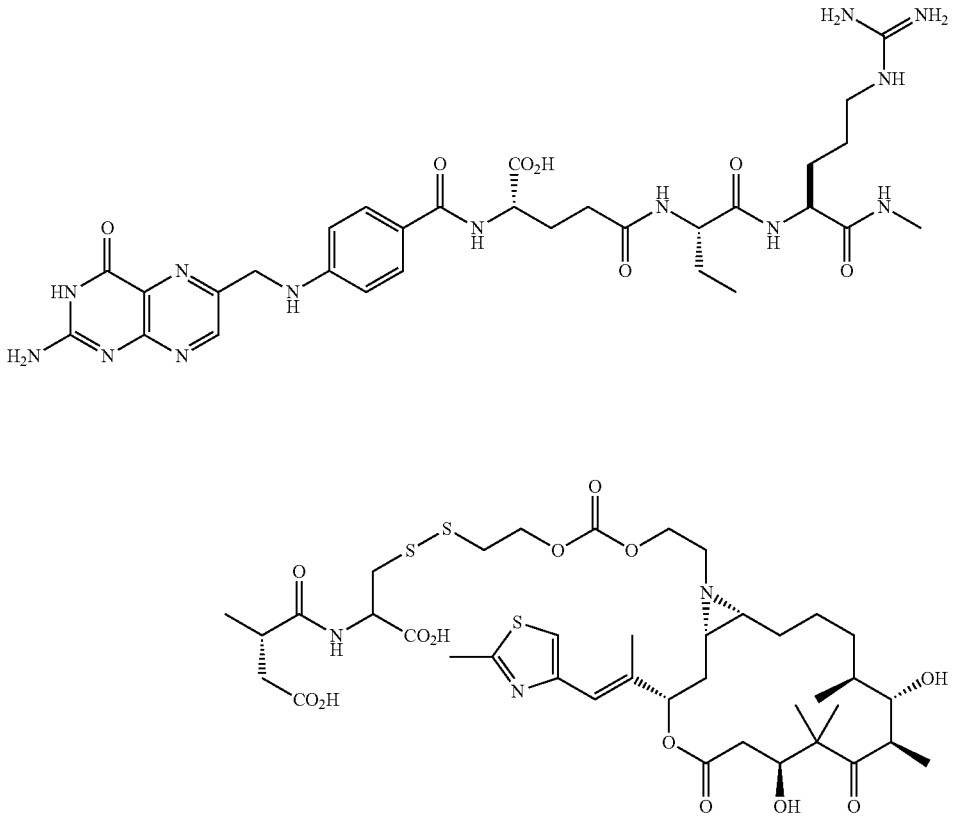

(S)-2-(4-((2-amino-4-oxo-3,4-dihydropteridin-6-yl)methylamino)benzamido)-5-((S)-3-carboxy-1-(S)-1-((S)-3-carboxy-1-((R)-1-carboxy-2-(2-(2-((2-((1S,3S,7S,10R,11S,12S, 16R)-7,11-dihydroxy-8,8,10,12-tetramethyl-3-((E)-1-(2-methylthiazol-4-yl)prop-1-en-2-yl)-5,9-dioxo-4-oxa-17-aza-bicyclo[14.1.0]heptadecan-17-yl)ethoxy)carbonyloxy)ethyl)disulfanyl)ethylamino)-1-oxopropan-2-ylamino)-5-guanidino-1-oxopentan-2-ylamino)-1-oxopropan-2-ylamino)-5-oxopentanoic acid A. [1S-[1R*,3R*(E),7R*,10S*,11R*,12R*,16S*]]-8,8,10,12-Tetramethyl-3-[1-methyl-2-(2-methyl-4-thiazolyl)ethenyl]-7,11-bis[(triethylsily)oxy]-4,17-dioxabicyclo[14.1.0]heptadecane-5,9-dione

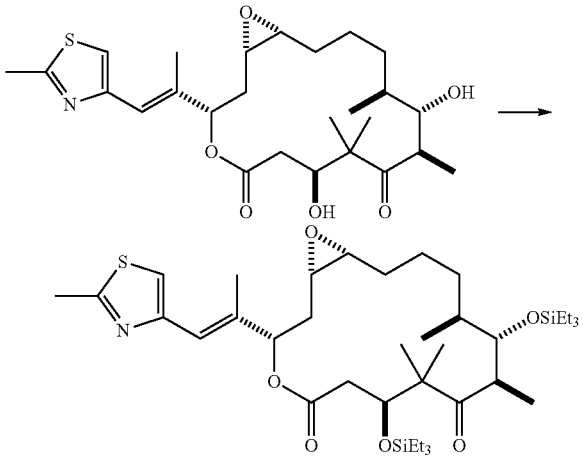

To a stirred solution of Epothilone A (5.0 g, 10.1 mmol), imidazole (3.40 g, 49.9 mmol) and DIPEA (28.5 mL, 163.6 mmol) in anhydrous DMF (100 mL) under $N_2$ atmosphere was added triethylsilyl chloride (15.0 mL, 89.4 mmol). After the addition was complete, the reaction solution was warmed at 55° C. (oil bath temperature) for 12 hr to give a single spot (tlc) of the desired product.

The above reaction was repeated two more times. The DMF of the combined solution was distilled under high vacuum. The foamy residue was purified by column chromatography (silica gel, E. Merck, 230-400 mesh, 600 g; 5:95, 10:90 and 15:85 EtOAc/hexanes) to give 19.4 g (88.6%) of Compound A as a white solid.

HPLC: ES Industries FluoroSep RP Phenyl, 4.6×250 mm, isocratic, 30 min, 100% B, (B=90% MeOH/$H_2O$+0.2% $H_3PO_4$), flow rate at 1.0 ml/min, UV 254, t=23.15 min. LC/MS (ES+) 722 (M+H).

B. Preparation of [4S-[4R*,7S*,8R*,9R*,13S*,14S*,16R*(E)]]-14-Bromo-13-hydroxy-5,5,7,9-tetramethyl-16-[1-methyl-2-(2-methyl-4-thiazolyl)ethenyl]-4,8-bis[(triethylsilyl)oxy]-1-oxacyclohexadecane-2,6-dione

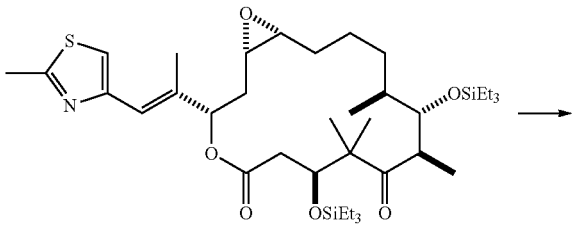

-continued

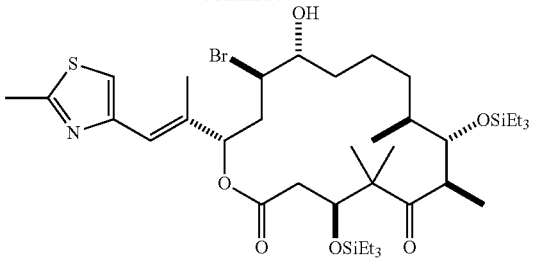

To a stirred solution of [1S-[1R*,3R*(E),7R*,10S*,11R*,12R*,16S*]]-8,8,10,12-Tetramethyl-3-[1-methyl-2-(2-methyl-4-thiazolyl)ethenyl]-7,11-bis[(triethylsily)oxy]-4,17-dioxabicyclo[14.1.0]heptadecane-5,9-dione (5.0 g, 6.92 mmol) in anhydrous dichloromethane (140 mL) at −20° C. under $N_2$ atmosphere was added $MgBr_2$-$Et_2O$ (3×2.13 g, 24.78 mmol) in three portions every two hours while maintaining an internal temperature below −5° C. After about 7 hr, the reaction mixture was diluted with dichloromethane and washed with sat. $NaHCO_3$ (2×), dried over anhydrous $Na_2SO_4$ and evaporated in vacuum to give a foam. The residue was purified by column chromatography (silica gel, E. Merck, 230-400 mesh, 180 g; 5:95, 7.5:92.5 and 12.5:87.5 EtOAc/hexanes) to give Compound B (2.5 g, 45% yield) as a white foam along with recovered starting material (0.9 g, 18%).

HPLC: ES Industries FluoroSep RP Phenyl, 4.6×250 mm, isocratic, 30 min, 100% B, (B=90% MeOH/$H_2O$+0.2% $H_3PO_4$), flow rate at 1.0 ml/min, UV 254, t=14.37 min.(100% pure) LC/MS (ES+): 802 (M+H).

C. Preparation of [4S-[4R*,7S*,8R*,9R*,13S*,14R*,16R*(E)]]-14-Azido-13-hydroxy-5,5,7,9-tetramethyl-16-[1-methyl-2-(2-methyl-4-thiazolyl)ethenyl]-4,8-bis[(triethylsilyl)oxy]-1-oxacyclohexadecane-2,6-dione

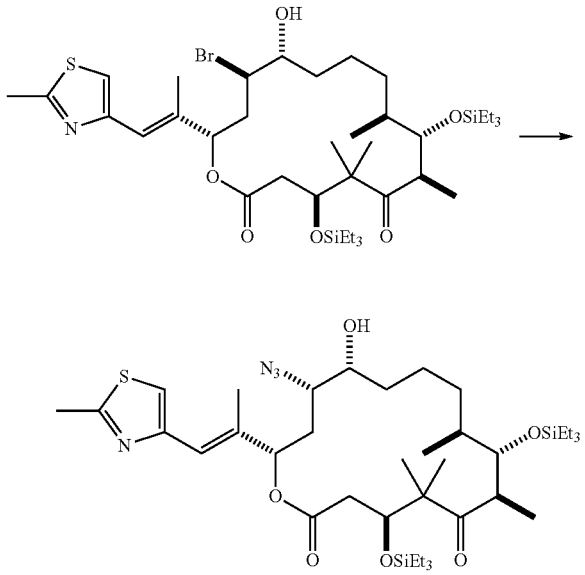

To a solution of [4S-[4R*,7S*,8R*,9R*,13S*,14S*,16R*(E)]]-14-Bromo-13-hydroxy-5,5,7,9-tetramethyl-16-[1-methyl-2-(2-methyl-4-thiazolyl)ethenyl]-4,8-bis[(triethylsilyl)oxy]-1-oxacyclohexadecane-2,6-dione (9.9 g, 12.3 mmol) in 1.2 L of DMF were added sodium azide (8.01 g, 123.3 mmol) and 18-crown-6 (3.26 g, 12.3 mmol) at RT under $N_2$ atmosphere. The clear solution was stirred mechanically at rt for 7 days. The solution was diluted with EtOAc (4 L), and washed with $H_2O$ (6×3 L). The organic layer was dried ($Na_2SO_4$), and then evaporated to give 9.2 g of the crude product. Column chromatography (silica gel 450 g, 5-15% EtOAc/hexane) furnished 6.7 g (71% yield) Compound C as a white foam.

HPLC: YMC ODS-A S5, 4.6×50 mm, isocratic, 30 min, 100% B. (B=90% MeOH/$H_2O$+0.2% $H_3PO_4$), flow rate at 4.0 mL/min, UV 254 nm, t=2.00 min LC/MS (ES+) 765 (M+H).

D. Preparation of [4S-[4R*,7S*,8R*,9R*,13R*,14R*,16R*(E)]]-14-Azido-5,5,7,9-tetramethyl-16-[1-methyl-2-(2-methyl-4-thiazoly)ethenyl]-13-[(4-nitrobenzoyl)oxy]-4,8-bis[(triethylsilyl)oxy]-1-oxacyclohexadecane-2,6-dione

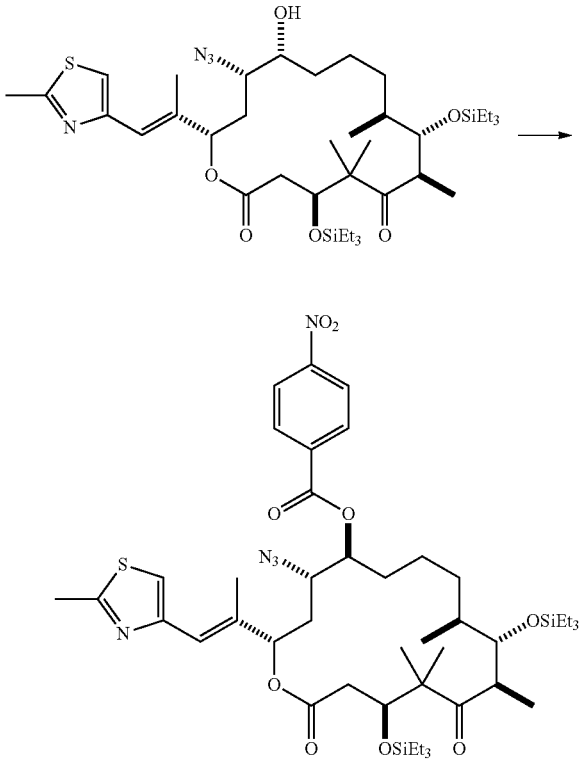

[4S-[4R*,7S*,8R*,9R*,13S*,14R*,16R*(E)]]-14-Azido-13-hydroxy-5,5,7,9-tetramethyl-16-[1-methyl-2-(2-methyl-4-thiazolyl)ethenyl]-4,8-bis[(triethylsilyl)oxy]-1-oxacyclohexadecane-2,6-dione (7.0 g, 9.15 mmol), 4-nitrobenzoic acid (3.82 g, 22.9 mmol), and triphenylphosphine (6.0 g, 22.9 mmol) were dissolved in THF (100 mL). Diethylazodicarboxylate (9.0 mL of 40% solution in toluene, 22.9 mmol) were added over a period of 5 minutes. The reaction mixture was maintained at RT for 4 hr, concentrated and purified by silica gel chromatography (stepwise gradient from 5% ethylacetate/hexanes to 15% ethylacetate/hexanes) to isolate the nitrobenzoate ester as a white foam (7.3 g, 87%).

LC-MS: Phenomenex C18, 4.6×50 mm, isocratic, 15 min, 100% B. (B=90% MeOH/$H_2O$+0.1% TFA), flow rate at 4.0 mL/min, UV 220 nm. Retention time=8.9 min. MS (ESI) M+H=886.7

E. Preparation of [4S-[4R*,7S*,8R*,9R*,13R*,14R*,16R*(E)]]-14-Azido-13-hydroxy-5,5,7,9-tetramethyl-16-[1-methyl-2-(2-methyl-4-thiazolyl)ethenyl]-4,8-bis[(triethylsilyl)oxy]-1-oxacyclohexadecane-2,6-dione

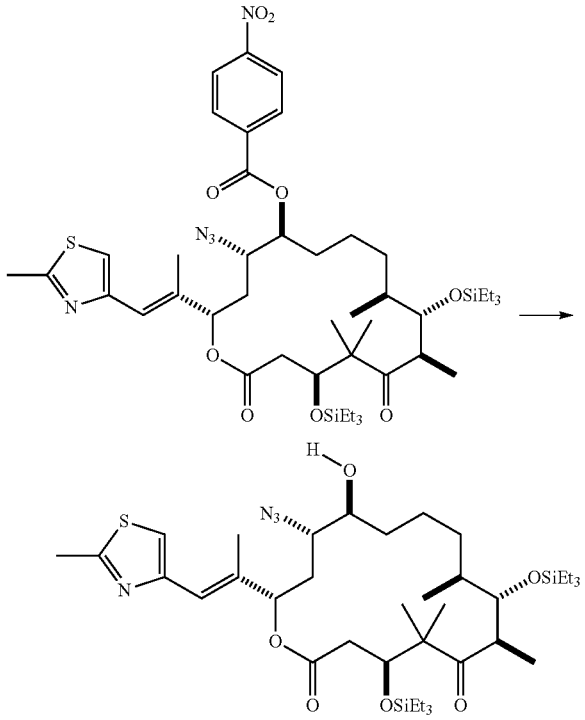

The nitrobenzoate ester Compound D (7.3 g, 7.98 mmol) was dissolved in ethyl acetate (35 mL) and cooled to 0° C. Ammonia in methanol (350 mL of 2M solution in methanol) was added, and the reaction mixture stirred at RT for 4 hr, concentrated and purified by silica gel chromatography (stepwise gradient from 10% ethylacetate/hexanes to 30% ethylacetate/hexanes) to isolate [4S-[4R*,7S*,8R*,9R*,13R*,14R*,16R*(E)]]-14-Azido-13-hydroxy-5,5,7,9-tetramethyl-16-[1-methyl-2-(2-methyl-4-thiazolyl)ethenyl]-4,8-bis[(triethylsilyl)oxy]-1-oxacyclohexadecane-2,6-dione as a glassy white solid (5.97 g, 98%).

LC-MS: Phenomenex C18, 4.6×50 mm, isocratic, 5 min, 100% B. (B=90% MeOH/$H_2O$+0.1% TFA), flow rate at 4.0 mL/min, UV 220 nm. Retention time=2.25 min MS (ESI) M+H=765.66

F. Preparation of [1S-[1R*,3R*(E),7R*,10S*,11R*,12R*,16S*]]-8,8,10,12-Tetramethyl-3-[1-methyl-2-(2-methyl-4-thiazolyl)ethenyl]-7,11-bis[(triethylsilyl)oxy]-4-oxa-17-azabicyclo[14.1.0]heptadecane-5,9-dione

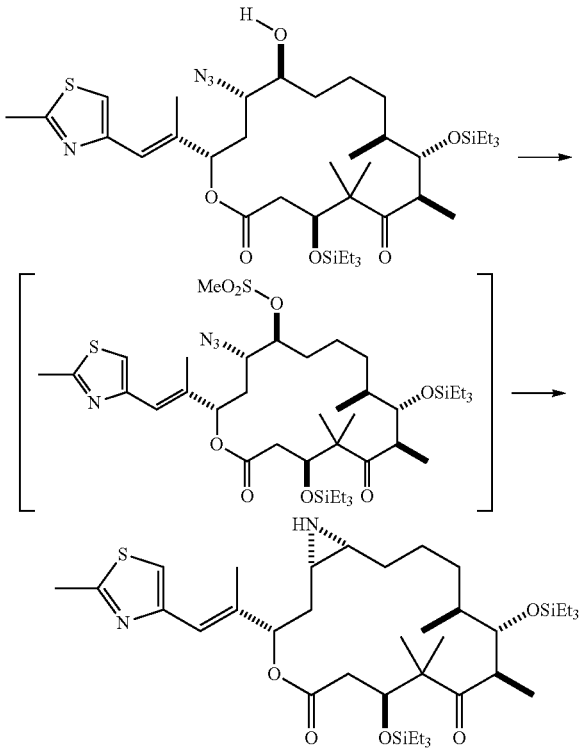

[4S-[4R*,7S*,8R*,9R*,13R*,14R*,16R*(E)]]-14-Azido-13-hydroxy-5,5,7,9-tetramethyl-16-[1-methyl-2-(2-methyl-4-thiazolyl)ethenyl]-4,8-bis[(triethylsilyl)oxy]-1-oxacyclohexadecane-2,6-dione (5.97 g, 7.8 mmol) and triethylamine (4.34 mL, 31.2 mmol) were dissolved in dichloromethane (85 mL) and cooled to 0° C. Methanesulfonylchloride (1.8 mL, 23.4 mmol) was added dropwise over a period of 5 min. After 10 min, the reaction mixture was removed from the ice bath, and stirred at RT. After 3 hr, the reaction mixture was taken-up in saturated $NaHCO_3$ (300 mL), extracted with dichloromethane (3×100 mL), dried over $Na_2SO_4$, concentrated and taken to next step without further purification.

The crude methanesulfonate ester was dissolved in THF/$H_2O$ (12:1, 130 mL). Triethylamine (2.2 mL, 16 mmol) and trimethylphosphine (16 mmol, 16 mL of 1.0 M solution in THF) were added, and the reaction mixture was stirred at RT. After 3 hr, the reaction was heated at 45° C. for 7 hr, concentrated and purified by silica gel chromatography (stepwise gradient from 2% methanol/chloroform to 5% methanol/chloroform) to isolate Compound F as a white solid (5.08 g, 88% for two steps).

LC-MS: Phenomenex C18, 4.6×50 mm, isocratic, 5 min, 100% B. (B=90% MeOH/$H_2O$+0.1% TFA), flow rate at 4.0 mL/min, UV 220 nm. Retention time=0.298 min. MS (ESI) M+H=721.58

G. Preparation of [1S-[1R*,3R*(E),7R*,10S*,11R*,12R*,16S*]]-7,11-Dihydroxy-17-[2-hydroxyethyl]-8,8,10,12-tetramethyl-3-[1-methyl-2-(2-methyl-4-thiazolyl)ethenyl]-4-oxa-17-azabicyclo[14.1.0]heptadecane-5,9-dione

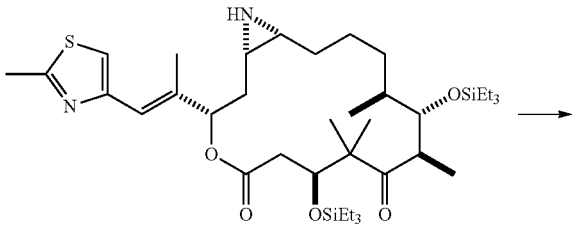

-continued

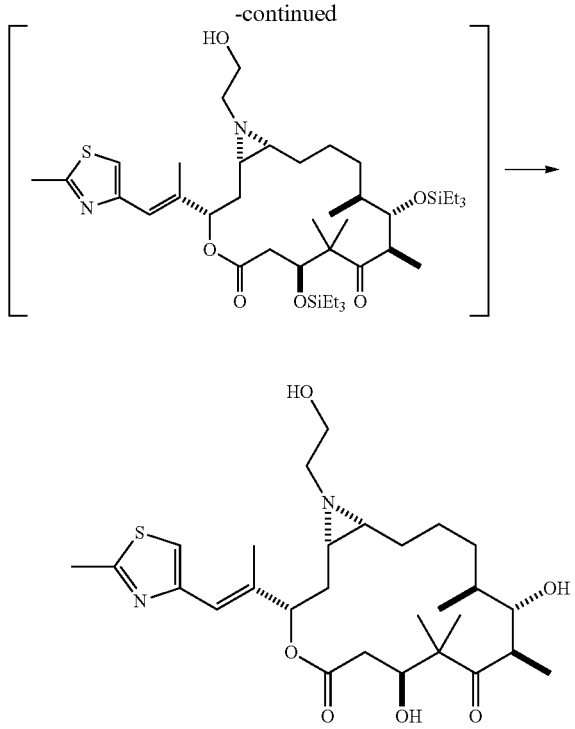

$K_2CO_3$ (1.4 g, 10.2 mmol) and 2-bromoethanol (0.52 mL, 7.3 mmol) were added to [1S-[1R*,3R*(E),7R*,10S*,11R*,12R*,16S]]-8,8,10,12-Tetramethyl-3-[1-methyl-2-(2-methyl-4-thiazolyl)ethenyl]-7,11-bis[(triethylsilyl)oxy]-4-oxa-17-azabicyclo[14.1.0]heptadecane-5,9-dione (1.05 g, 1.46 mmol) in acetonitrile (20 mL) and heated to 82° C. After 4 hr, additional 2-bromoethanol (0.52 mL, 7.3 mmol) and $K_2CO_3$ (1.4 g, 10.2 mmol) were added. After 5 hr, additional 2-bromoethanol (0.21 mL, 2.92 mmol) was added. After 3 hr, the reaction mixture was cooled to room temperature, filtered through Celite, washed with acetonitrile (5×5 mL), dichloromethane (2×5 mL), concentrated and taken to next step without further purification.

The crude reaction product was dissolved in dichloromethane (40 mL), cooled to 0° C., and trifluoroacetic acid (8.0 mL) was added. After 1 hr, the reaction mixture was concentrated, taken-up in saturated $NaHCO_3$ (200 mL), extracted with dichloromethane (3×100 mL), dried over $Na_2SO_4$, concentrated, and purified by silica gel chromatography (10% methanol/dichloromethane) to isolate [1S-[1R*,3R*(E),7R*,10S*,11R*,12R*,16S*]]-7,11-Dihydroxy-17-[2-hydroxyethyl]-8,8,10,12-tetramethyl-3-[1-methyl-2-(2-methyl-4-thiazolyl)ethenyl]-4-oxa-17-azabicyclo[14.1.0]heptadecane-5,9-dione (Compound G), as a clear film (0.62 g, 79% for two steps).

LC-MS: Waters Sunfire C18, 4.6×50 mm, gradient, 0 to 100% B over 4 min. (A=10% MeOH/$H_2O$+0.1% TFA; B=90% MeOH/$H_2O$+0.1% TFA), flow rate at 4.0 mL/min, UV 220 nm. Retention time=2.12 min. MS (ESI) M+H=537.52.

H. Preparation of (S)-2-(4-((2-amino-4-oxo-3,4-dihydropteridin-6-yl)methylamino)benzamido)-5-((S)-3-carboxy-1-((S)-1-((S)-3-carboxy-1-((S)-1-carboxy-2-mercaptoethylamino)-1-oxopropan-2-ylamino)-5-guanidino-1-oxopentan-2-ylamino)-1-oxopropan-2-ylamino)-5-oxopentanoic acid

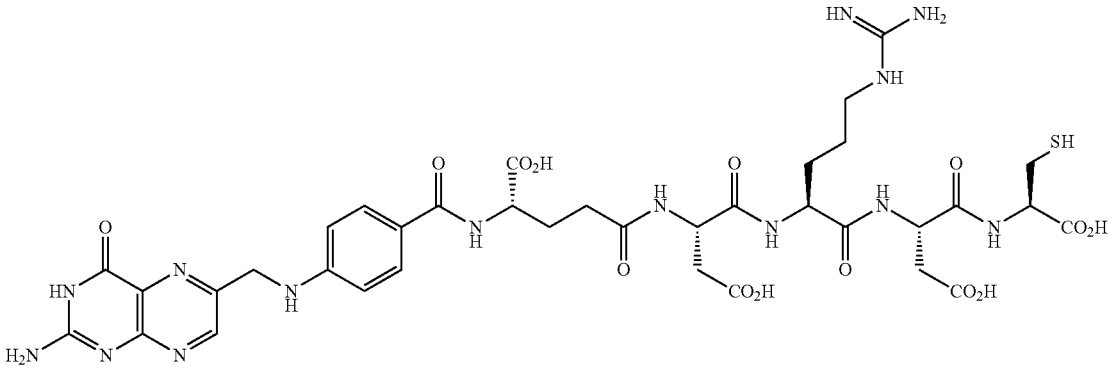

(S)-2-(4-((2-amino-4-oxo-3,4-dihydropteridin-6-yl)methylamino)benzamido)-5-((S)-3-carboxy-1-(S)-1-(S)-3-carboxy-1-((S)-1-carboxy-2-mercaptoethylamino)-1-oxopropan-2-ylamino)-5-guanidino-1-oxopentan-2-ylamino)-1-oxopropan-2-ylamino)-5-oxopentanoic acid was synthesized by solid phase peptide synthesis in five steps starting from H-Cys(4-methoxytrityl)-2-chlorotrityl-resin. The Table 2 shows the amount of reagents used in the synthesis.

TABLE 2

| | Mmol | Equiv. | MW | amount |
|---|---|---|---|---|
| H-Cys(4-methoxytrityl)-2-chlorotrityl-Resin (loading 0.57 mmol/g) | 1.14 | | | 2.0 g |
| Fmoc-Asp(OtBu)-OH (dissolve in 15 mL DMF) | 1.14 | 2 | 411.5 | 0.938 g |
| Fmoc-Arg(Pbf)-OH (15 mL DMF) | 1.14 | 2 | 648 | 1.477 g |
| Fmoc-Asp(OtBu)-OH (dissolve in 15 mL DMF) | 1.14 | 2 | 411.5 | 0.938 g |
| Fmoc-Glu-OtBu (15 mL DMF) | 1.14 | 2 | 425.5 | 0.970 g |
| $N^{10}$TFA Pteroic Acid (dissolve in 15 mL DMSO) | 1.14 | 1.25 | 408 | 0.581 g |
| DIPEA | 1.14 | 4 | 174 | 0.793 |
| PyBOP | 1.14 | 2 | 520 | 1.185 g |

The following procedures were used:

Coupling steps:

To the resin in a peptide synthesis vessel were added the amino acid solution, DIPEA, and PyBOP. The mixture was bubbled for 1 hr and washed 3× with DMF and isopropyl alcohol. FMOC deprotection was effected by treatment with 20% piperidine in DMF, 2× (10 min), before each amino acid coupling. This sequence was repeated for each amino acid coupling step.

Synthesis of $N^{10}$-TFA-protected pteroic acid:

To 10 L of 0.1 M tris base solution (121.1 g tris base in 10 L water) in a 22 L mechanically-stirred round bottomed flask, equipped with a heating mantle, was added 200 g (0.453 mole) of folic acid. The mixture was stirred to dissolve the folic acid, and then 500 mg (3.67 mmole) zinc chloride was added. Carboxypeptidase G (13×20 unit vials available from Sigma) was added and the pH was adjusted to 7.3 with 1N HCl and maintained throughout the reaction. The mixture was protected from light and heated at 30° C. for 8-10 days (use of an auto-titrator to hold the pH constant reduced the conversion time by 4-5 days). The reaction was monitored by analytical HPLC until 80% conversion was achieved (further conversion is desirable but has not been optimized). The product was precipitated from the reaction mixture by adjusting the solution to pH=3.0 using 6N HCl. The slurry was transferred to a centrifuge vial and centrifuged at 4000 rpm for 10 min. The supernatant was decanted. The wet solid was then directly purified as follows (the wet solid could be frozen for storage or first freeze-dried; however, storage of wet solids in the freezer until dissolution was more efficient). To 40 g of crude pteroic acid in 700 mL of water was added 1.0 M NaOH until pH=11.5. The mixture was filtered (Whatman type 1) and then chromatographed (column: 10×120 cm; stationary phase: 8 kg DEAE cellulose; mobile phase: 1.0 M NaCl/0.01 M NaOH, pH=11.5; flow rate: 17 ml/min). One liter yellow-colored fractions were collected and analyzed by HPLC. Fractions containing pure pteroic acid were adjusted to pH=3 with 6 M HCl to precipitate pteroic acid. The mixture was centrifuged at 3000 rpm for 20 min. The supernatant was decanted and washed with water (3×). The solid was freeze-dried for at least 72 hr. The impact of residual water on the next reaction is not known.

The pteroic acid was further dried over $P_2O_5$ under high vacuum for over 24 hr (note that similar results in the protection step were obtained without this additional drying step). Next, 100 g (0.32 mol) of pteroic acid was added to a 5 L round bottom flask, equipped with a mechanical stirrer and an argon inlet, and stored under high vacuum overnight. Argon gas was added followed by 3500 g (2316 mL) of trifluoroacetic anhydride. The flask was sealed with a rubber stopper or argon inlet adaptor, and then stirred vigorously. The flask was protected from light and stirred at room temperature under argon atmosphere for 7 days (the reaction was monitored by HPLC of aliquots diluted 20× each with water and DMSO). The mixture was rotary evaporated to dryness and treated with 2.5 L of 3% trifluoroacetic acid in water. The mixture was stirred overnight at room temperature to hydrolyze anhydride by-products. Rotary evaporation gave a dry solid. The solid was suspended in 2 L of water and then centrifuged in 250-mL centrifuge bottles at 3000 rpm for 20 min. The supernatant was removed and the solid was washed with water and centrifuged (4 times). The solid was freeze-dried for 3 days, transferred to amber bottles, and dried under high vacuum in the presence of $P_2O_5$ for 2 days (Purity≧95%; residual TFA assessed by Elemental Analysis).

Cleavage step:

The protected intermediate was released from the resin using the cleavage reagent prepared from 92.5% (50 mL) TFA, 2.5% (1.34 mL) $H_2O$, 2.5% (1.34 mL) Triisopropylsilane, and 2.5% (1.34 mL) ethanedithiol. The cleavage reagent was added to the reaction vessel (25 mL). Argon was bubbled through the mixture for 1.5 hr. The liquid was drained from the vessel, and resin was washed with remaining reagent (3×8 mL). The volatiles were concentrated by rotary evaporation to a volume of 10 mL. Diethyl ether (35.0 mL) was added to effect precipitation. The solid was collected by centrifugation and dried to give 1.25 g of cleavage product.

Deprotection Step:

The $N^{10}$-trifluoroacetyl protecting group in the pteroic acid portion was removed under basic conditions. Starting with 250 mg of protected intermediate in 10 mL water, the pH was adjusted to 9.3 and maintained for 1 hr using 4:1$H_2O$:ammonium hydroxide (1-2 mL). After 1 hr, the pH was adjusted to 5 with 1N HCl (~1 mL) and the product was purified on preparative HPLC to yield 125 mg of Compound H.

HPLC Purification Conditions:

Column: Waters NovaPak $C_{18}$ 300×9 mm

Solvent A: Buffer 10 mM Ammonium Acetate, pH=5

Solvent B: Acetonitrile

Elution: 1% B to 20% B in 40 min at 15 mL/min

Total yield from combined reactions: 625 mg

I. Preparation of 2-((1S,3S,7S,10R,11S,12S,16R)-7,11-dihydroxy-8,8,10,12-tetramethyl-3-((E)-1-(2-methylthiazol-4-yl)prop-1-en-2-yl)-5,9-dioxo-4-oxa-17-aza-bicyclo[14.1.0]heptadecan-17-yl)ethyl 2-(2-(pyridin-2-yl)disulfanyl)ethyl carbonate 1. Preparation of 2-(2-(Pyridin-2-yl)disulfanyl)ethanol

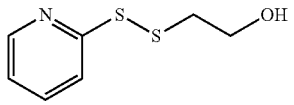

To a solution of methoxycarbonyl sulfenyl chloride (10 mL, 110 mmol), in dichloromethane (100 mL), cooled to 0 C, was added mercaptoethanol (7.6 mL, 110 mmol), dropwise. The reaction mixture was allowed to stir at 0° C. for 30 min. At this point, a solution of 2-mercaptopyridine (12.2 g, 110 mmol) in dichloromethane (160 mL) was added. The solution was allowed to react at 0° C. for 1 hr and then was allowed to warm to RT for another 1 hr. Solid product was observed to have fallen out of solution. TLC (1:1 Pet Ether/EtOAc) showed that significant product had been formed. The reaction mixture was concentrated to a volume of 125 mL. The mixture was filtered through a Buchner funnel. The filter cake was washed with dichloromethane and then dried under vacuum overnight to afford 2-(2-(Pyridin-2-yl)disulfanyl) ethanol (23.6 g), as the HCl salt.

TLC: $R_f$=0.45

Plates—EMD Silica Gel 60 $F_{254}$, 5×10 cm, 250 M

2. Preparation of Benzo[d][1,2,3]triazol-1-yl 2-(2-(pyridin-2-yl)disulfanyl)ethyl carbonate

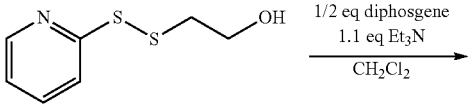

-continued

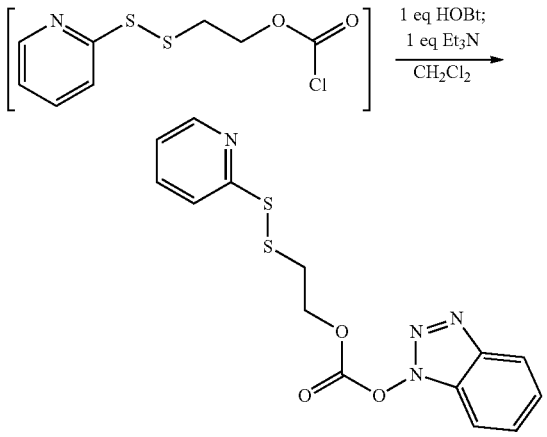

HCL salt

A solution of diphosgene (2.28 g, 11.5 mmol) in 15 mL anhydrous dichloromethane was stirred under argon in a roundbottom flask and cooled by a ice/salt bath. An addition funnel with a mixture of 2-(pyridin-2-yldisulfanyl)ethanol (5.01 g, 22.4 mmol) and triethylamine (2.25 g, 22.2 mmol) in 65 mL anhydrous dichloromethane was placed onto the roundbottom flask. The mixture was added dropwise over a period of 20 min. The reaction mixture was allowed to warm to RT and stirred for an additional 1 hr. TLC analysis of the reaction mixture showed that the starting material was consumed and there was formation of a "streaking" less polar chloroformate product, TLC (6:4 EtOAc:Hexanes): $R_F$ of starting material 0.4; $R_F$ of chloroformate product: 0.8.

The reaction mixture was stirred in a roundbottom flask under argon and cooled by an ice/salt bath. A mixture of 3.02 g, 22.4 mmol HOBt and 2.23 g, 22.0 mmol triethylamine in 10 mL anhydrous dichloromethane was added to a dropping funnel affixed to the roundbottom flask. The mixture was slowly added to the roundbottom flask maintaining the reaction temperature at 2° C. The reaction mixture was allowed to warm to RT and stirred overnight. Approximately 27 mL of dichloromethane was then distilled from the reaction mixture at atmospheric pressure. The mixture was then allowed to cool to RT and stir for 2 hr. The solids were collected by filtration, and the filter cake was washed with 20 mL of dichloromethane. The solids were then dried under vacuum at 40° C. on a rotary evaporator to afford 7.81 g of off-white solids. This product was analyzed by 1H-NMR and determined to be the desired product.

3. Preparation of 2-((1S,3S,7S,10R,11S,12S,16R)-7,11-dihydroxy-8,8,10,12-tetramethyl-3-((E)-1-(2-methylthiazol-4-yl)prop-1-en-2-yl)-5,9-dioxo-4-oxa-17-aza-bicyclo[14.1.0]heptadecan-17-yl)ethyl 2-(2-(pyridin-2-yl)disulfanyl)ethyl carbonate

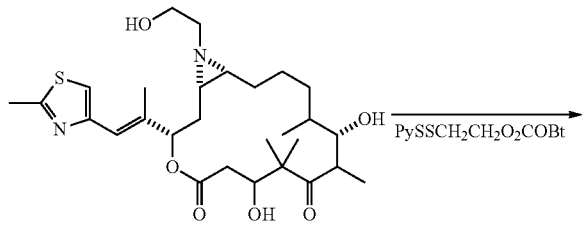

-continued

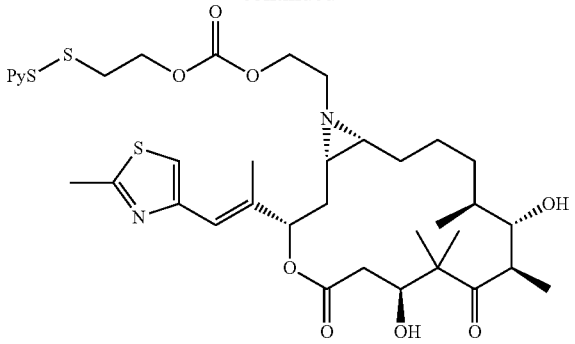

To a solution of [1S-[1R*,3R*(E),7R*,10S*,11R*,12R*,16S*]]-7,11-Dihydroxy-17-[2-hydroxyethyl]-8,8,10,12-tetramethyl-3-[1-methyl-2-(2-methyl-4-thiazolyl)ethenyl]-4-oxa-17-azabicyclo[14.1.0]heptadecane-5,9-dione in anhydrous dichloromethane at 0° C. was added DMAP (1.2 eq.) and benzo[d][1,2,3]triazol-1-yl 2-(2-(pyridin-2-yl)disulfanyl)ethyl carbonate (1.0 eq.) in tandem. The reaction mixture was stirred at 0° C. under argon and monitored by TLC every 10 min. Additional DMAP (1.2 eq.) and Compound I (2)(1.0 eq.) were added as necessary until all of Compound G was consumed. The reaction was quenched with MeOH (1 mL) at 0° C., the solvent was removed under vacuum, and the residue was purified by chromatography (silica gel, 2.5-5% MeOH in DCM) to afford the title compound as a beige solid. Compound amounts and recoveries are listed below in Table 3. Total yield from 2.95 g of Compound G was 2.80 g (67.9%) of Compound I.

TABLE 3

| | Compound G (mg) | Compound I (2) (mg) | DMAP (mg) | DCM (mL) | Compound I (mg)* |
|---|---|---|---|---|---|
| Batch #1 | 303 | 197 × 3 | 82.8 × 3 | 8.0 | 204 |
| Batch #2 | 952 | 683 × 3 | 260 × 3 | 22.0 | 984 |
| Batch #3 | 921 | 661 × 3 | 251 × 3 | 22.0 | 761 |
| Batch #4 | 775 | 556 × 3 | 211 × 3 | 18.0 | 851 |

*Each chromatographic purification typically gave pure product along with some impure (80-90% purity) product. The impure product was combined with the crude product from the next batch for chromatographic purification. For batches #2 and 4, two chromatographic purifications were carried out.

J. Preparation of (S)-2-(4-((2-amino-4-oxo-3,4-dihydropteridin-6-yl)methylamino)benzamido)-5-((S)-3-carboxy-1-((S)-1-((S)-3-carboxy-1-((R)-1-carboxy-2-(2-(2-((2-((1S,3S,7S,10R,11S,12S,16R)-7,11-dihydroxy-8,8,10,12-tetramethyl-3-((E)-1-(2-methylthiazol-4-yl)prop-1-en-2-yl)-5,9-dioxo-4-oxa-17-aza-bicyclo[14.1.0]heptadecan-17-yl)ethoxy)carbonyloxy)ethyl)disulfanyl)ethylamino)-1-oxopropan-2-ylamino)-5-guanidino-1-oxopentan-2-ylamino)-1-oxopropan-2-ylamino)-5-oxopentanoic acid

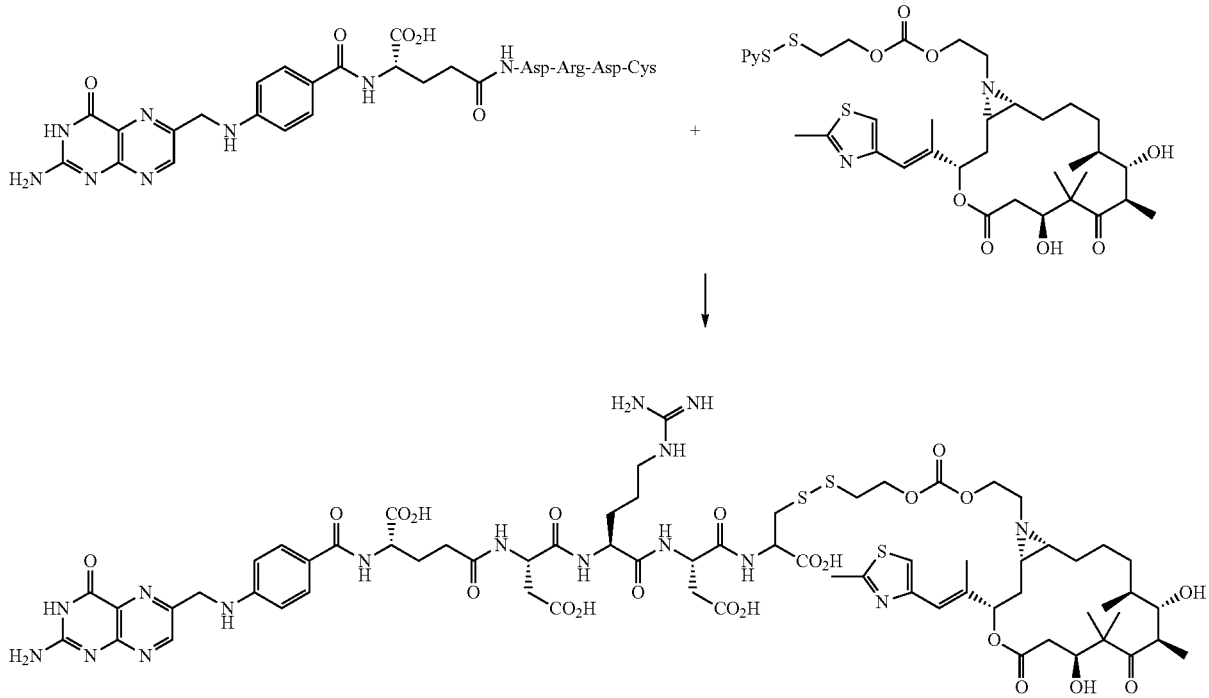

To 15 mL of $H_2O$ (bubbled with argon for 10 min before use) was added to (S)-2-(4-((2-amino-4-oxo-3,4-dihydropteridin-6-yl)methylamino)benzamido)-5-((S)-3-carboxy-1-((S)-1-((S)-3-carboxy-1-((S)-1-carboxy-2-mercaptoethylamino)-1-oxopropan-2-ylamino)-5-guanidino-1-oxopentan-2-ylamino)-1-oxopropan-2-ylamino)-5-oxopentanoic acid (498 mg, 0.534 mmol) in a 50 mL size centrifuge tube. To this suspension, while bubbling with argon, was added dropwise saturated $NaHCO_3$ solution (bubbled with argon for 10 min before use) until the pH of the resulting solution reached 6.9. 2-((1S,3S,7S,10R,11S,12S,16R)-7,11-dihydroxy-8,8,10,12-tetramethyl-3-((E)-1-(2-methylthiazol-4-yl)prop-1-en-2-yl)-5,9-dioxo-4-oxa-17-aza-bicyclo[14.1.0]heptadecan-17-yl)ethyl 2-(2-(pyridin-2-yl)disulfanyl)ethyl carbonate (400 mg, 0.534 mmol) in THF was added quickly and the resulting homogenous solution was stirred under argon for 30 min. The reaction progress was checked by analytical HPLC at 15 min. The product peak came out at ~6.4 min under analytical HPLC conditions. The mixture was diluted with ~15 mL of phosphate buffer and the THF was removed under vacuum. The cloudy solution was centrifuged and filtered. The yellow filtrate was divided into two portions and purified by preparative HPLC. Pure fractions (>98% pure) were pooled and freeze-dried. Tail fractions (<98% pure) were collected and re-purified for every 3-6 chromatography runs to provide 700 mg of the title compound as a white powder (contains 11.8% by weight of water and 8.7% by weight sodium and sodium phosphate salts, as determined by Karl Fischer and elemental analyses).

Preparative HPLC Parameters:

Column: Waters Nova-Pak HR C18 6 μm 30×300 mm

Mobile phase A: 7.0 mM sodium phosphate buffer, pH=7.2

Mobile phase B: acetonitrile

Method: 10% B-50% B in 30 min, flow rate: 40 mL/min

Analytical HPLC Parameters:

Column: Waters Symmetry C18 3.5 μm 4.6×75 mm

Mobile phase A: 10 mM Triethylammonium acetate (TEAOAc) buffer, pH=7.5

Mobile phase B: Acetonitrile

Method: 20% B-40% B in 10 min, flow rate: 1.0 mL/min

Accurate mass m/z ($C_{67}H_{92}N_{16}O_{22}S_3$):

Calculated: 1570.58907 (M+2H), 785.29454 $(M+2H)^{2+}$, 523.86563 $(M+3H)^{3+}$, 393.15118 $(M+4H)^{4+}$ Found: $(M+2H)^{2+}$ at 785.29100 (4.5 ppm), $(M+3H)^{3+}$ at 523.86431 (2.5 ppm), $(M+4H)^{4+}$ at 393.14996 (3.1 ppm)

Example 3

Alternative Preparation of Compound J (S)-2-(4-((2-amino-4-oxo-3,4-dihydropteridin-6-yl)methylamino)benzamido)-5-((S)-3-carboxy-1-((S)-1-((S)-3-carboxy-1-((R)-1-carboxy-2-(2-(2-((2-((1S,3S,7S,10R,11S,12S,16R)-7,11-dihydroxy-8,8,10,12-tetramethyl-3-((E)-1-(2-methylthiazol-4-yl)prop-1-en-2-yl)-5,9-dioxo-4-oxa-17-aza-bicyclo[14.1.0]heptadecan-17-yl) ethoxy)carbonyloxy)ethyl)disulfanyl)ethylamino)-1-oxopropan-2-ylamino)-5-guanidino-1-oxopentan-2-ylamino)-1-oxopropan-2-ylamino)-5-oxopentanoic acid 3A. Preparation of [4S,7R,8S,10R,9S,13R,16S]-4,8,13-trihydroxy-14-iodo-5,5,7,9-tetramethyl-16-[(E)-1-[2-methylthiazol-4-yl]prop-1-en-2-yl]oxacyclohexadecane-2,6-dione

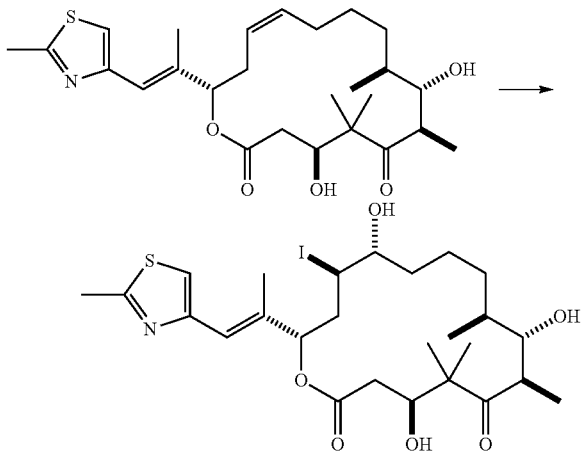

Epothilone C (54.3 g, 113.7 mmol) was dissolved in acetonitrile (480 mL) and water (50 mL). The solution was cooled to −5° C. to −10° C. Iodine (144.3 g, 568.4 mmol) was added to the reaction and the reaction was held at least for 15 hr.

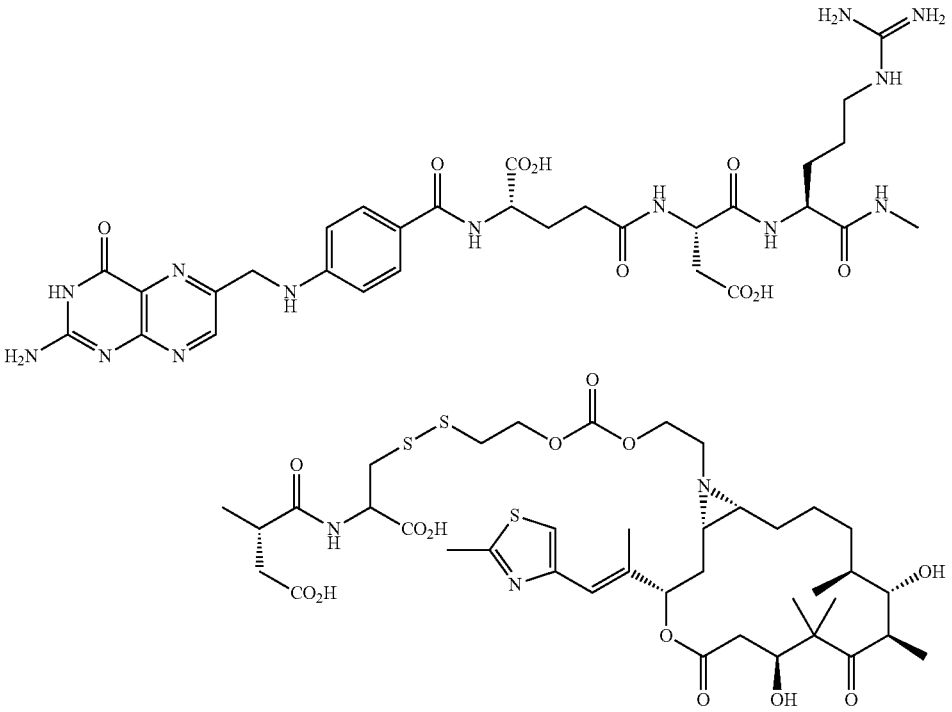

The reaction was quenched with 15% sodium metabisulfite solution (900 mL). The mixture was extracted with ethyl acetate (2×1.1 L). Organic phases were collected and washed successively with saturated sodium bicarbonate solution (675 mL) and saturated sodium chloride solution (675 mL). The solvents were evaporated under reduced pressure to give crude Compound A as yellow oil (85.6 g). The Compound A was used in next reaction without further purification.

HPLC: Phenomex Luna C8 (2) 3 um, 4.6×150 mm, isocratic, 18 min, 36% B, 17 min, 56% B, (Mobile phase A=0.01M NH4OAc in ACN:Water (5:95), Mobile phase B=0.01M NH4OAc in ACN:Water (95:5)), flow rate at 1.0 ml/min, UV 245, Rt=22.4 min.

3B. Preparation of [1R,3S,7S,10R,11S,12S,16S]-7,11-dihydroxy-8,8,10,12-tetramethyl-3-[(E)-1-[2-methylthiazol-4-yl]prop-1-en-2-yl]-4,17-dioxabicyclo[14.1.0]heptadecane-5,9-dione.

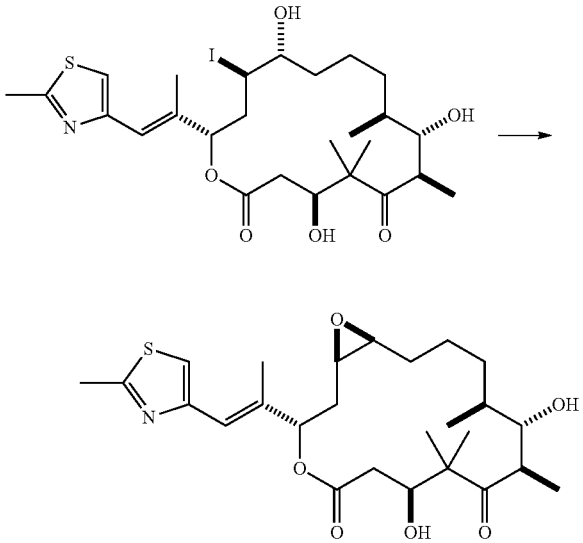

[4S,7R,8S,10R,9S,13R,16S]-4,8,13-trihydroxy-14-iodo-5,5,7,9-tetramethyl-16-[(E)-1-[2-methylthiazol-4-yl]prop-1-en-2-yl]oxacyclohexadecane-2,6-dione (85.6 g) was dissolved in acetonitrile (670 mL) and water (130 mL). Triethylamine (135 mL, 968.5 mmol) was added to the solution. The reaction was heated to 50° C. to 60° C. for at least 8 hr.

After it was cooled to RT, the solution was concentrated under reduced pressure. The residue was diluted with EtOAc (1.2 L) and washed with saturated sodium chloride solution (3×500 mL). The solvents were evaporated under reduced pressure to give the crude product as yellow oil. Purification by silica gel pad filtration (silica gel 700 g, 66% EtOAc in heptane, 2×4 L, and 1×3 L) afforded Compound B as foam (50.3 g, 90% yield) with HPLC AP 80. HPLC: Phenomex Luna C8 (2)3 um, 4.6×150 mm, isocratic, 18 min, 36% B, 17 min, 56% B, (Mobile phase A=0.01M NH4OAc in ACN:Water (5:95), Mobile phase B=0.01 M NH4OAc in ACN:Water (95:5)), flow rate at 1.0 ml/min, UV 245, Rt=15.0 min.

3C/3D. Preparation of (4S,7R,8S,9S,13R,14R,16S)-13-Azido-4,8,14-trihydroxy-5,5,7,9-tetramethyl-16-((E)-1-(2-methylthiazol-4-yl)prop-1-en-2-yl)oxacyclohexadecane-2,6-dione and (4S,7R,8S,9S,13S,14S,16S)-14-Azido-4,8,13-trihydroxy-5,5,7,9-tetramethyl-16-((E)-1-(2-methylthiazol-4-yl)prop-1-en-2-yl)oxacyclohexadecane-2,6-dione.

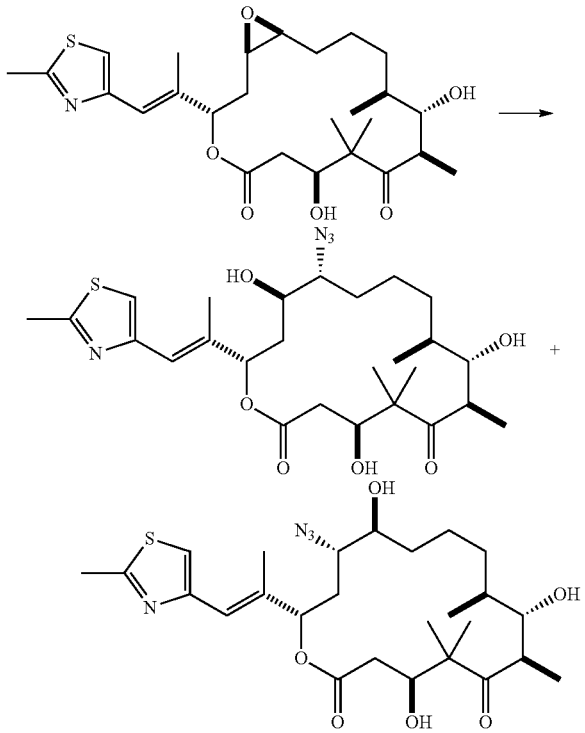

6:1 ratio

To a stirred solution of epi-Epothilone-A (14.35 g, 29.07 mmol) in ethanol (240 mL) and water (48 mL) was added sodium azide (11.45 g, 174.41 mmol) and ammonium chloride (3.14 g, 58.14 mmol). The mixture was stirred at 60° C. for 17-20 h. Volatiles were evaporated on the rotary evaporator under reduced pressure below 50° C. The residue was dissolved in ethyl acetate (287 mL) and water (50 mL) mixture. Phases were separated and the bottom aqueous phase was extracted with ethyl acetate (115 mL). The combined organic phases were washed with 25% aqueous sodium chloride (brine) solution. Solvent was evaporated under reduced pressure and the residue was passed through a pad of silica gel eluting with ethyl acetate/n-heptane (2:1) mixture. Evaporation of the solvent under reduced pressure provided regioisomeric mixture of azido-alcohols, (4S,7R,8S,9S,13R,14R,16S)-13-Azido-4,8,14-trihydroxy-5,5,7,9-tetramethyl-16-((E)-1-(2-methylthiazol-4-yl)prop-1-en-2-yl) oxacyclohexadecane-2,6-dione and (4S,7R,8S,9S,13S,14S,16S)-14-Azido-4,8,13-trihydroxy-5,5,7,9-tetramethyl-16-((E)-1-(2-methylthiazol-4-yl)prop-1-en-2-yl) oxacyclohexadecane-2,6-dione in ~6:1 ratio (12.8 g, 82%) as a white foam.

LC-MS: Phenomenex Luna C8(2) column: 3 μm, 4.6×50 mm. Gradient: 15 min, 0% B to 100% B in 10 min, then 100% B for 5 min. Mobile phases: A=0.01 M $NH_4OAc$ in $CH_3CN/H_2O$ 5:95; B=0.01 M $NH_4OAc$ in $CH_3CN/H_2O$ 95:5. Flow rate: 3.0 mL/min. Wavelength: UV 250 nm. Retention time=5.52 min. MS (ESI) $(M+H)^+$=537.69

This reaction also works in other solvents like, acetone, acetonitrile, tetrahydrofuran, 2-propanol, dimethylformamide, methylsulfoxide and N-methylpyrrolidinone.

Tertrabutylammonium azide reagent also can be used instead of sodium azide/ammonium chloride 3E. Preparation of (1S,3S,7S,10R,11S,12S16R)-7,11-dihydroxy-8,8,10,12-tetramethyl-3-((E)-1-(2-methylthiazol-4-yl)prop-1-en-2-yl)-4-oxa-17-azabicyclo(14.1.0)heptadecane-5,9-dione.

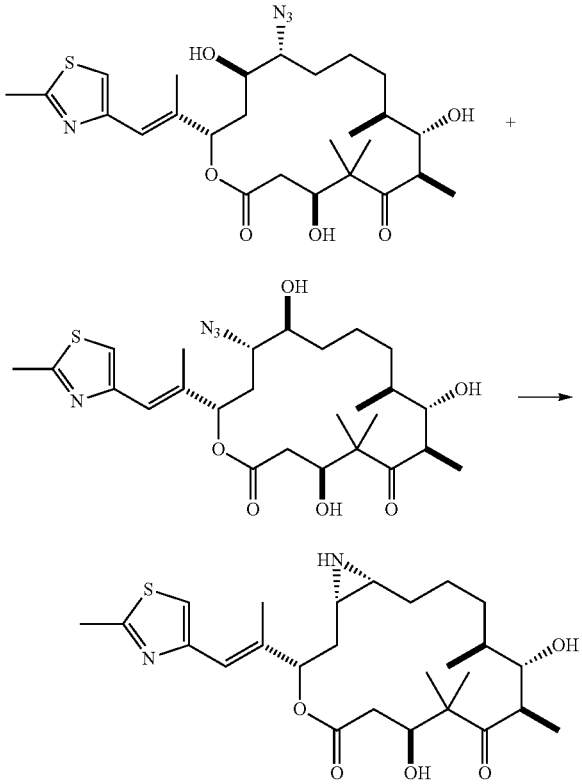

To a stirred solution of (4S,7R,8S,9S,13R,14R,16S)-13-Azido-4,8,14-trihydroxy-5,5,7,9-tetramethyl-16-((E)-1-(2-methylthiazol-4-yl)prop-1-en-2-yl)oxacyclohexadecane-2,6-dione and (4S,7R,8S,9S,13S,14S,16S)-14-Azido-4,8,13-trihydroxy-5,5,7,9-tetramethyl-16-((E)-1-(2-methylthiazol-4-yl)prop-1-en-2-yl)oxacyclohexadecane-2,6-dione mixture (12.8 g, 23.85 mmol) in anhydrous acetonitrile (90 mL) was added triphenylphosphine (9.48 g, 35.77 mmol) under nitrogen atmosphere. The clear solution was stirred at 20-40° C. for 19-40 h. The reaction mixture was cooled to 0-5° C. for 3-4 h and filtered the product. The cake was washed with heptane (64 mL) and dried at 40° C. under reduced pressure for 15-18 h to give (1S,3S,7S,10R,11S,12S16R)-7,11-dihydroxy-8,8,10,12-tetramethyl-3-((E)-1-(2-methylthiazol-4-yl)prop-1-en-2-yl)-4-oxa-17-azabicyclo(14.1.0)heptadecane-5,9-dione as a white solid (5.41 g, 46%). LC-MS: Phenomenex Luna C8(2) column: 3 μm, 4.6×50 mm. Gradient: 15 min, 0% B to 100% B in 10 min, then 100% B for 5 min. Mobile phases: A=0.01 M $NH_4OAc$ in $CH_3CN/H_2O$ 5:95; B=0.01 M $NH_4OAc$ in $CH_3CN/H_2O$ 95:5. Flow rate: 3.0 mL/min. Wavelength: UV 250 nm. Retention time=4.43 min. MS (ESI) $(M+H)^+$=493.68

This reaction also works with other phosphines like, tricyclohexylphosphine, trimethylphosphine, tributylphosphine and tris(4-methoxyphenyl)-phosphine and another solvent tetrahydrofuran.

3G. Preparation of [1S-[1R*,3R*(E),7R*,10S*,11R*,12R*,16S*]]-7,11-Dihydroxy-17-[2-hydroxyethyl]-8,8,10,12-tetramethyl-3-[1-methyl-2-(2-methyl-4-thiazolyl)ethenyl]-4-oxa-17-azabicyclo[14.1.0]heptadecane-5,9-dione

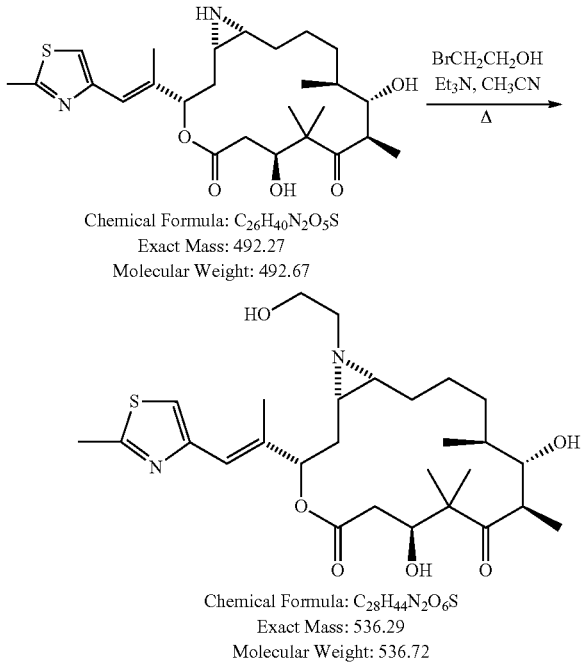

$Et_3N$ (4.95 mL, 35.52 mmol) and 2-bromoethanol (3.02 mL, 42.62 mmol) were added to (1S,3S,7S,10R,11S,12S,16R)-7,11-dihydroxy-8,8,10,12-tetramethyl-3-((E)-1-(2-methylthiazol-4-yl)prop-1-en-2-yl)-4-oxa-17-azabicyclo[14.1.0]heptadecane-5,9-dione (3.50 g, 7.10 mmol) in acetonitrile (35 mL) and heated to 72.5° C. After 20 hr, the reaction mixture was cooled to room temperature, concentrated to dryness through rotary vacuum distillation. The crude was dissolved in ethyl acetate (50 mL) and mixed with deionized water (35 mL). The mixture was extracted with ethyl acetate (3×35 mL), dried over $Na_2SO_4$, filtered, concentrated, crystallized in acetonitrile (35 mL), washed with acetonitrile (2×5 mL), and dried in vacuum oven at 45.5° C. overnight to isolate (1S,3S,7S, 10R,11S,12S,16R)-7,11-dihydroxy-17-(2-hydroxyethyl)-8,8,10,12-tetramethyl-3-((E)-1-(2-methylthiazol-4-yl)prop-1-en-2-yl)-4-oxa-17-azabicyclo[14.1.0]heptadecane-5,9-dione as a white crystalline powder (2.60 g, HPLC AP 97.1, 68.2% yield).

LC-MS: Phenomenex C8, 3 μm, 4.6×150 mm, gradient, 10 to 50% B over 10 min, and stop at 20 min. (A=5% MeCN/$H_2O$+0.01 M $NH_4OAc$; B=95% MeOH/$H_2O$+0.01 M $NH_4OAc$), flow rate at 1.0 mL/min, UV 254 nm. Retention time=9.43 min. MS (ESI) M+H=537.21.

An ordinarily skilled artisan will recognize that Compound 3G as prepared by this Example 3 is identical to Compound G as prepared by Example 2, and thus, Compound 3G may be used to prepare Compounds H, I, and J, the methods of preparation and compounds of which are described in Example 2.

We claim:

1. A compound having the formula X:

X

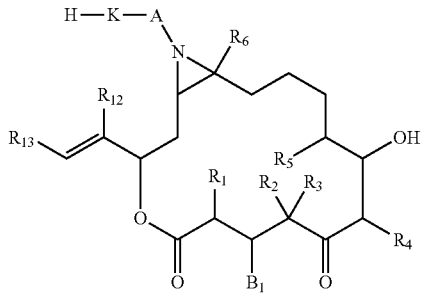

or a pharmaceutically-acceptable salt thereof, wherein:

K is —O—;

A is $C_{2-4}$ alkylene;

$B_1$ is —OH and $R_1$ is hydrogen;

$R_2$, $R_3$, $R_4$, and $R_5$ are, independently, hydrogen or lower alkyl;

$R_6$ is hydrogen or methyl;

$R_{12}$ is H, alkyl, substituted alkyl, or halogen; and $R_{13}$ is an optionally substituted 5 or 6 membered heteroaryl.

2. A compound according to claim 1, wherein $R_6$ is hydrogen.

3. A compound according to claim 1, wherein $R_6$ is methyl.

4. A compound according to claim 1 wherein $R_{13}$ is an optionally substituted thiazolyl, pyridyl, or oxazolyl.

5. A compound according to claim 1, having the formula b,

Xb

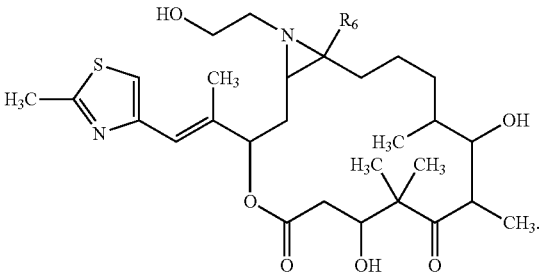

6. A compound according to claim 5, wherein $R_6$ is hydrogen.

7. A compound according to claim 5, wherein $R_6$ is methyl.

8. A compound according to claim 5, having the formula Xb':

Xb′

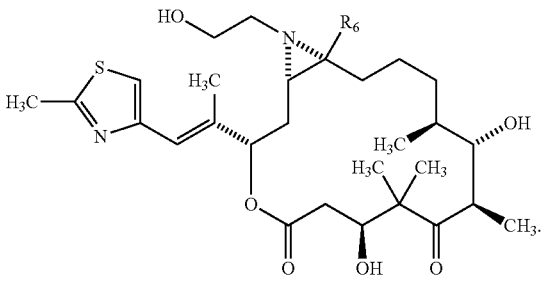

9. A compound according to claim 8, wherein $R_6$ is hydrogen.

10. A compound according to claim 1, having the formula X':

X′

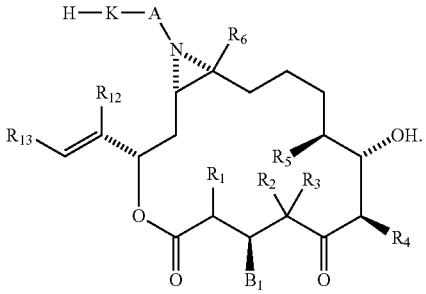

* * * * *